(12) United States Patent
Margeot et al.

(10) Patent No.: US 10,000,780 B2
(45) Date of Patent: Jun. 19, 2018

(54) ENDOGLUCANASE VARIANTS HAVING IMPROVED ACTIVITY, AND USES OF SAME

(71) Applicants: IFP ENERGIES NOUVELLES, Rueil Malmaison (FR); PROTEUS, Longjumeau (FR); CENTRE NATIONAL DE LA RECHERCHE SCIENTIFIQUE—CNRS, Paris (FR)

(72) Inventors: Antoine Margeot, Paris (FR); Yves Benoit, Pierrelaye (FR); Cecile Persillon, Nimes (FR); Celine Ayrinhac, Domessargues (FR); Christophe Ullmann, Nimes (FR); Olivier Bonzom, Nimes (FR); Sebastien Fort, Vaulnaveys-le-Haut (FR); Sylvie Armand, Grenoble (FR); Maud Petit, Marcq en Baroeul (FR); Marine Lenon, Sassenage (FR)

(73) Assignees: IFP ENERGIES NOUVELLES, Rueil Malmaison (FR); PROTEUS, Longjumeau (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days. days.

(21) Appl. No.: 15/038,580

(22) PCT Filed: Nov. 21, 2014

(86) PCT No.: PCT/FR2014/052984
§ 371 (c)(1),
(2) Date: May 23, 2016

(87) PCT Pub. No.: WO2015/075391
PCT Pub. Date: May 28, 2015

(65) Prior Publication Data
US 2016/0298156 A1     Oct. 13, 2016

(30) Foreign Application Priority Data
Nov. 22, 2013  (FR) ...................... 13 61509

(51) Int. Cl.
| | | |
|---|---|---|
| *C12N 9/14* | (2006.01) | |
| *C12P 19/14* | (2006.01) | |
| *C12P 19/02* | (2006.01) | |
| *C12N 9/42* | (2006.01) | |
| *C12P 7/10* | (2006.01) | |
| *C12P 7/14* | (2006.01) | |

(52) U.S. Cl.
CPC ............ *C12P 19/14* (2013.01); *C12N 9/2437* (2013.01); *C12P 7/10* (2013.01); *C12P 7/14* (2013.01); *C12P 19/02* (2013.01); *C12Y 302/01004* (2013.01); *Y02E 50/16* (2013.01)

(58) Field of Classification Search
CPC ..................................................... C12P 19/02
USPC ......................................................... 435/195
See application file for complete search history.

(56) References Cited

FOREIGN PATENT DOCUMENTS

| | | |
|---|---|---|
| WO | 2008/148131 | 12/2008 |
| WO | 2009/085935 | 7/2009 |
| WO | 2010/088387 | 5/2010 |
| WO | 2011/057140 | 5/2011 |
| WO | 2011/059740 | 5/2011 |
| WO | 2011/153516 | 12/2011 |
| WO | 2012/036810 | 3/2012 |
| WO | 2012/044915 | 4/2012 |
| WO | 2013/028701 | 2/2013 |

OTHER PUBLICATIONS

Accession No. P07981 (Aug. 1, 1988).*
Akcapinar, Gunseli Bayram et al., "From in silica to in vitro: Modelling and production of Trichoderma reesei endoglucanase 1 and its mutant in Pichia pastoris" Journal of Biotechnology (2012), vol. 159, pp. 61-68.
The International Search Report (ISR) with Written Opinion for PCT/FR2014/052984 dated Mar. 5, 2015, pp. 1-16.
English Translation of the ISR for PCT/FR2014/052984 dated Mar. 5, 2015, pp. 1-6.

* cited by examiner

*Primary Examiner* — Tekchand Saidha
(74) *Attorney, Agent, or Firm* — McDonnell Boehnen Hulbert & Berghoff LLP

(57) ABSTRACT

Disclosed are variants of *Trichoderma reesei* endoglucanase I, and methods for using such variants to break down cellulose and produce biofuel.

16 Claims, 3 Drawing Sheets

SEQUENCE LISTING

```
<160> NUMBER OF SEQ ID NOS: 30

<210> SEQ ID NO 1
<211> LENGTH: 1380
<212> TYPE: DNA
<213> ORGANISM: Trichoderma reesei

<400> SEQUENCE: 1
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccgggggtgt cgtggcccag gacacctcgg tggtccttga ctggaactac     180
cgctggatgc acgacgcaaa ctacaactcg tgcaccgtca acggcggcgt caacaccacg     240
ctctgccctg acgaggcgac ctgtggcaag aactgcttca tcgagggcgt cgactacgcc     300
gcctcgggcg tcacgacctc gggcagcagc ctcaccatga accagtacat gcccagcagc     360
tctggcggct acagcagcgt ctctcctcgg ctgtatctcc tggactctga cggtgagtac     420
gtgatgctga agctcaacgg ccaggagctg agcttcgacg tcgacctctc tgctctgccg     480
tgtggagaga acggctcgct ctacctgtct cagatggacg agaacggggg cgccaaccag     540
tataacacgg ccggtgccaa ctacgggagc ggctactgcg atgctcagtg ccccgtccag     600
acatggagga acggcaccct caacactagc caccagggct tctgctgcaa cgagatggat     660
atcctggagg gcaactcgag ggcgaatgcc ttaccccctc actcttgcac ggccacggcc     720
tgcgactctg ccggttgcgg cttcaacccc tatggcagcg gctacaaaag ctactacggc     780
cccggagata ccgttgacac ctccaagacc ttcaccatca tcacccagtt caacacggac     840
aacggctcgc cctcgggcaa ccttgtgagc atcacccgca agtaccagca aaacggcgtc     900
gacatcccca gcgcccagcc cggcggcgac accatctcgt cctgcccgtc cgcctcagcc     960
tacggcggcc tcgccaccat gggcaaggcc ctgagcagcg gcatggtgct cgtgttcagc    1020
atttggaacg acaacagcca gtacatgaac tggctcgaca gcggcaacgc cggccctgc    1080 agcagcaccg agggcaaccc atccaacatc ctggccaaca ccccaacac gcacgtcgtc    1140 ttctccaaca tccgctgggg agacattggg tctactacga actcgactgc gccccgcc    1200 ccgcctgcgt ccagcacgac gttttcgact acacggagga gctcgacgac ttcgagcagc    1260
ccgagctgca cgcagactca ctgggggcag tgcggtggca ttgggtacag cgggtgcaag    1320
acgtgcacgt cgggcactac gtgccagtat agcaacgact actactcgca atgcctttaa    1380

<210> SEQ ID NO 2
```

```
<211> LENGTH: 459
<212> TYPE: PRT
<213> ORGANISM: Trichoderma reesei

<400> SEQUENCE: 2
```

| | | | | | | | | | | | | | | | |
|---|---|---|---|---|---|---|---|---|---|---|---|---|---|---|---|
|Met|Ala|Pro|Ser|Val|Thr|Leu|Pro|Leu|Thr|Thr|Ala|Ile|Leu|Ala|Ile|
|1| | | |5| | | | |10| | | | |15| |
|Ala|Arg|Leu|Val|Ala|Ala|Gln|Gln|Pro|Gly|Thr|Ser|Thr|Pro|Glu|Val|
| | | |20| | | | |25| | | | |30| | |
|His|Pro|Lys|Leu|Thr|Thr|Tyr|Lys|Cys|Thr|Lys|Ser|Gly|Gly|Cys|Val|
| | |35| | | | |40| | | | |45| | | |
|Ala|Gln|Asp|Thr|Ser|Val|Val|Leu|Asp|Trp|Asn|Tyr|Arg|Trp|Met|His|
| |50| | | | |55| | | | |60| | | | |
|Asp|Ala|Asn|Tyr|Asn|Ser|Cys|Thr|Val|Asn|Gly|Gly|Val|Asn|Thr|Thr|
|65| | | | |70| | | | |75| | | | |80|
|Leu|Cys|Pro|Asp|Glu|Ala|Thr|Cys|Gly|Lys|Asn|Cys|Phe|Ile|Glu|Gly|
| | | | |85| | | | |90| | | | |95| |
|Val|Asp|Tyr|Ala|Ala|Ser|Gly|Val|Thr|Thr|Ser|Gly|Ser|Ser|Leu|Thr|
| | | |100| | | | |105| | | | |110| | |
|Met|Asn|Gln|Tyr|Met|Pro|Ser|Ser|Gly|Gly|Tyr|Ser|Ser|Val|Ser|
| | |115| | | | |120| | | | |125| | | |
|Pro|Arg|Leu|Tyr|Leu|Leu|Asp|Ser|Asp|Gly|Glu|Tyr|Val|Met|Leu|Lys|
| |130| | | | |135| | | | |140| | | | |
|Leu|Asn|Gly|Gln|Glu|Leu|Ser|Phe|Asp|Val|Asp|Leu|Ser|Ala|Leu|Pro|
|145| | | | |150| | | | |155| | | | |160|
|Cys|Gly|Glu|Asn|Gly|Ser|Leu|Tyr|Leu|Ser|Gln|Met|Asp|Glu|Asn|Gly|
| | | | |165| | | | |170| | | | |175| |
|Gly|Ala|Asn|Gln|Tyr|Asn|Thr|Ala|Gly|Ala|Asn|Tyr|Gly|Ser|Gly|Tyr|
| | | |180| | | | |185| | | | |190| | |
|Cys|Asp|Ala|Gln|Cys|Pro|Val|Gln|Thr|Trp|Arg|Asn|Gly|Thr|Leu|Asn|
| | |195| | | | |200| | | | |205| | | |
|Thr|Ser|His|Gln|Gly|Phe|Cys|Cys|Asn|Glu|Met|Asp|Ile|Leu|Glu|Gly|
| |210| | | | |215| | | | |220| | | | |
|Asn|Ser|Arg|Ala|Asn|Ala|Leu|Thr|Pro|His|Ser|Cys|Thr|Ala|Thr|Ala|
|225| | | | |230| | | | |235| | | | |240|
|Cys|Asp|Ser|Ala|Gly|Cys|Gly|Phe|Asn|Pro|Tyr|Gly|Ser|Gly|Tyr|Lys|
| | | | |245| | | | |250| | | | |255| |
|Ser|Tyr|Tyr|Gly|Pro|Gly|Asp|Thr|Val|Asp|Thr|Ser|Lys|Thr|Phe|Thr|
| | | |260| | | | |265| | | | |270| | |
|Ile|Ile|Thr|Gln|Phe|Asn|Thr|Asp|Asn|Gly|Ser|Pro|Ser|Gly|Asn|Leu|
| | |275| | | | |280| | | | |285| | | |
|Val|Ser|Ile|Thr|Arg|Lys|Tyr|Gln|Gln|Asn|Gly|Val|Asp|Ile|Pro|Ser|
| |290| | | | |295| | | | |300| | | | |
|Ala|Gln|Pro|Gly|Gly|Asp|Thr|Ile|Ser|Ser|Cys|Pro|Ser|Ala|Ser|Ala|
|305| | | | |310| | | | |315| | | | |320|
|Tyr|Gly|Gly|Leu|Ala|Thr|Met|Gly|Lys|Ala|Leu|Ser|Ser|Gly|Met|Val|
| | | | |325| | | | |330| | | | |335| |
|Leu|Val|Phe|Ser|Ile|Trp|Asn|Asp|Asn|Ser|Gln|Tyr|Met|Asn|Trp|Leu|
| | | |340| | | | |345| | | | |350| | |
|Asp|Ser|Gly|Asn|Ala|Gly|Pro|Cys|Ser|Ser|Thr|Glu|Gly|Asn|Pro|Ser|
| | |355| | | | |360| | | | |365| | | |
|Asn|Ile|Leu|Ala|Asn|Asn|Pro|Asn|Thr|His|Val|Val|Phe|Ser|Asn|Ile|
| |370| | | | |375| | | | |380| | | | |
|Arg|Trp|Gly|Asp|Ile|Gly|Ser|Thr|Thr|Asn|Ser|Thr|Ala|Pro|Pro|Pro|

```
              385                 390                 395                 400
Pro Pro Ala Ser Ser Thr Thr Phe Ser Thr Thr Arg Arg Ser Ser Thr
                    405                 410                 415

Thr Ser Ser Ser Pro Ser Cys Thr Gln Thr His Trp Gly Gln Cys Gly
                420                 425                 430

Gly Ile Gly Tyr Ser Gly Cys Lys Thr Cys Thr Ser Gly Thr Thr Cys
            435                 440                 445

Gln Tyr Ser Asn Asp Tyr Tyr Ser Gln Cys Leu
        450                 455

<210> SEQ ID NO 3
<211> LENGTH: 1329
<212> TYPE: DNA
<213> ORGANISM: Artificial Sequence
<220> FEATURE:
<223> OTHER INFORMATION: 76B4

<400> SEQUENCE: 3
cagcaaccgg gttcggtgac ccccgaggtc catcccaagt tgcccacctg gcagtgtaca      60
aagtccgggg ggtgcgtgga gcaggacacc tcggtggtcc ttgactggaa ctaccgctgg     120
ttccacacct cggacaacac cacctcgtgc accacgtcct cgggcatcga ctcgacgctc     180
tgccctgacg cagcgacctg tgccgagaac tgcgtcgtgg agggcaccga ctacaccagc     240
tcgggcatcg agacctcggg cagcagcctc accctgaggc agttcgtcaa ggacagcgag     300
ggcaagacca cagcgtctc tcctcgggcc tatctcctgg gcgccgacgg tgactacgtg     360
atgttcaagc tcctcaacca ggagctgagc ttcgacgtcg acgtctctac gctgccgtgt     420
ggagagaacg cagcgctcta cttctctgag atggacaaga ccgggggccg gaacgagcac     480
aacacgggcg gtgccaagta cgggagcggc tactgcgatg ctcagtgccc cgtccagaca     540
tggaacaacg gcaccctcaa cactagccac cagggctcgt gctgcaacga gatggatatc     600
ctggaggcca actcgagggc gaattcgtac ccccctcacc cctgcagtgc cacggactgc     660
gacaagggcg gttgcggctt caaccccctat gctctcggcc aaaaaagcta ctggggcccc     720
ggaggcaccg ttgacacctc caagcccttc accatcacca cccagttcat cacgaacgac     780
ggcaccacca ccggcaccct ttccgaaatc cgccgccagt acatgcaaaa cggcaaggtg     840
atcgccaatg ccgtttcctc cactggcgtc aactccatca ccgaggactg gtgcacgtcc     900
gtcgacggct cggccgccac ctttggcggc ctcaccacca tgggcaaggc cctgggccgc     960
ggcatggtgc tcatcttcag catttggaac gacgccagcg gctttatgaa ctggctcgac    1020
agcggcaacg ccggcccctg cagcagcacc gagggcaacc cagacttgat caaggcccag    1080
aaccccacga cgcacgtcgt cttctccaac atccgctggg gagacattgg gtctactttc    1140
aagggttctg atggctcggt gacgacgacg acgtcgacta catcgaccaa gaccacgact    1200
tcgaccgcgc cggggccaac gcagactcac tatgggcagt gcggtggcca agggtggact    1260
gggcccacgg cttgcgcatc gccctacacg tgccaggttc tgaacccgtg gtactcgcaa    1320
tgcctttaa                                                            1329

<210> SEQ ID NO 4
<211> LENGTH: 442
<212> TYPE: PRT
<213> ORGANISM: Artificial Sequence
<220> FEATURE:
<223> OTHER INFORMATION: 76B4

<400> SEQUENCE: 4
```

```
Gln Gln Pro Gly Ser Val Thr Pro Glu Val His Pro Lys Leu Pro Thr
1               5                   10                  15
Trp Gln Cys Thr Lys Ser Gly Gly Cys Val Glu Gln Asp Thr Ser Val
                20                  25                  30
Val Leu Asp Trp Asn Tyr Arg Trp Phe His Thr Ser Asn Thr Thr
        35                  40                  45
Ser Cys Thr Thr Ser Ser Gly Ile Asp Ser Thr Leu Cys Pro Asp Ala
    50                  55                  60
Ala Thr Cys Ala Glu Asn Cys Val Val Glu Gly Thr Asp Tyr Thr Ser
65                  70                  75                  80
Ser Gly Ile Glu Thr Ser Gly Ser Ser Leu Thr Leu Arg Gln Phe Val
                85                  90                  95
Lys Asp Ser Glu Gly Lys Thr Asn Ser Val Ser Pro Arg Ala Tyr Leu
                100                 105                 110
Leu Gly Ala Asp Gly Asp Tyr Val Met Phe Lys Leu Leu Asn Gln Glu
        115                 120                 125
Leu Ser Phe Asp Val Asp Val Ser Thr Leu Pro Cys Gly Glu Asn Ala
    130                 135                 140
Ala Leu Tyr Phe Ser Glu Met Asp Lys Thr Gly Gly Arg Asn Glu His
145                 150                 155                 160
Asn Thr Gly Gly Ala Lys Tyr Gly Ser Gly Tyr Cys Asp Ala Gln Cys
                165                 170                 175
Pro Val Gln Thr Trp Asn Asn Gly Thr Leu Asn Thr Ser His Gln Gly
                180                 185                 190
Ser Cys Cys Asn Glu Met Asp Ile Leu Glu Ala Asn Ser Arg Ala Asn
        195                 200                 205
Ser Tyr Thr Pro His Pro Cys Ser Ala Thr Asp Cys Asp Lys Gly Gly
    210                 215                 220
Cys Gly Phe Asn Pro Tyr Ala Leu Gly Gln Lys Ser Tyr Trp Gly Pro
225                 230                 235                 240
Gly Gly Thr Val Asp Thr Ser Lys Pro Phe Thr Ile Thr Thr Gln Phe
                245                 250                 255
Ile Thr Asn Asp Gly Thr Thr Thr Gly Thr Leu Ser Glu Ile Arg Arg
                260                 265                 270
Gln Tyr Met Gln Asn Gly Lys Val Ile Ala Asn Ala Val Ser Ser Thr
            275                 280                 285
Gly Val Asn Ser Ile Thr Glu Asp Trp Cys Thr Ser Val Asp Gly Ser
        290                 295                 300
Ala Ala Thr Phe Gly Gly Leu Thr Thr Met Gly Lys Ala Leu Gly Arg
305                 310                 315                 320
Gly Met Val Leu Ile Phe Ser Ile Trp Asn Asp Ala Ser Gly Phe Met
                325                 330                 335
Asn Trp Leu Asp Ser Gly Asn Ala Gly Pro Cys Ser Ser Thr Glu Gly
                340                 345                 350
Asn Pro Asp Leu Ile Lys Ala Gln Asn Pro Thr Thr His Val Val Phe
            355                 360                 365
Ser Asn Ile Arg Trp Gly Asp Ile Gly Ser Thr Phe Lys Gly Ser Asp
        370                 375                 380
Gly Ser Val Thr Thr Thr Thr Ser Thr Thr Ser Thr Lys Thr Thr Thr
385                 390                 395                 400
Ser Thr Ala Pro Gly Pro Thr Gln Thr His Tyr Gly Gln Cys Gly Gly
                405                 410                 415
```

```
Gln Gly Trp Thr Gly Pro Thr Ala Cys Ala Ser Pro Tyr Thr Cys Gln
            420                 425                 430

Val Leu Asn Pro Trp Tyr Ser Gln Cys Leu
        435                 440
```

<210> SEQ ID NO 5
<211> LENGTH: 1338
<212> TYPE: DNA
<213> ORGANISM: Artificial Sequence
<220> FEATURE:
<223> OTHER INFORMATION: 105F11

<400> SEQUENCE: 5

```
cagcaaccgg gtaccagcac ccccgaggtc catcccaagt tgacaaccta caagtgtaca    60
aagtccgggg gtgcgtggc ccaggacacc tcggtggtcc ttgactggaa ctaccactgg   120
attcacacgg tcgatgggta cacatcgtgc accacatcgt ccggcgtcga cagcacgctc   180
tgccctgacg cggcgacctg tgcgaagaac tgcgtgatcg agccggccaa ctacaccagc   240
gccggcgtca cgacctcggg cgacagcctc accatgtacc agtacgttca gagcaacggc   300
gtctacacca cgcctctcc tcggctgtat ctcctgggcc cgacaagaa ctacgtgatg    360
ctgaagctcc taggccagga gctgaccttc gacgtcgacc tctctgctct gccgtgtgga   420
gagaacggct cgctctacct gtctcagatg gacgagaacg ggggcgccaa ccagtataac   480
acggccggtg ccaactacgg gagcggctac tgcgatgctc agtgccccgt ccagacatgg   540
aggaacggca ccctcaacac tagccaccag ggctcgtgct gcaacgagat ggatatcctg   600
gaggccaact cgaaggcgga agccttcacc cctcacccct gcatcggcga caactgcgac   660
aagggcggtt gcggcttcaa ccctatgct ctcggccaaa aaagctactg ggccccgga    720
ggcaccgttg acacctccaa gcccttcacc atcaccaccc agttcatcac gaacgacggc   780
accaccaccg cacccttc cgaaatccgc cgccagtaca tgcaaaacgg caaggtgatc   840
gccaatgccg tttcctccac tggcgtcaac tccatcaccg aggactggtg cacgtccgtc   900
gacggctcgg ccgccacctt tggcggcctc accaccatgg gcaaggccct gggccgcggc   960
atggtgctcg tgttcagcat ttggaacgac aacagccagt acatgaactg gctcgacagc  1020
ggcaacgccg gcccctgcag cagcaccgag ggcaacccat ccaacatcct ggccaacaac  1080
cccaacacgc acgtcgtctt ctccaacatc cgctggggag acattgggtc tactacgaac  1140
tcgactgcgc ccccgcccc gcctgcgtcc agcacgacgt ttttcgactac acggaggagc  1200
tcgacgactt cgagcagccc gagctgcacg cagactcact gggggcagtg cggtggcatt  1260
gggtacagcg ggtgcaagac gtgcacgtcg ggcactacgt gccagtatag caacgactac  1320
tactcgcaat gcctttaa                                                1338
```

<210> SEQ ID NO 6
<211> LENGTH: 445
<212> TYPE: PRT
<213> ORGANISM: Artificial Sequence
<220> FEATURE:
<223> OTHER INFORMATION: 105F11

<400> SEQUENCE: 6

```
Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
            20                  25                  30

Val Leu Asp Trp Asn Tyr His Trp Ile His Thr Val Asp Gly Tyr Thr
```

```
              35                  40                  45
Ser Cys Thr Thr Ser Ser Gly Val Asp Ser Thr Leu Cys Pro Asp Ala
 50                  55                  60

Ala Thr Cys Ala Lys Asn Cys Val Ile Glu Pro Ala Asn Tyr Thr Ser
 65                  70                  75                  80

Ala Gly Val Thr Thr Ser Gly Asp Ser Leu Thr Met Tyr Gln Tyr Val
                 85                  90                  95

Gln Ser Asn Gly Val Tyr Thr Asn Ala Ser Pro Arg Leu Tyr Leu Leu
                100                 105                 110

Gly Pro Asp Lys Asn Tyr Val Met Leu Lys Leu Leu Gly Gln Glu Leu
                115                 120                 125

Thr Phe Asp Val Asp Leu Ser Ala Leu Pro Cys Gly Glu Asn Gly Ser
                130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175

Val Gln Thr Trp Arg Asn Gly Thr Leu Asn Thr Ser His Gln Gly Ser
                180                 185                 190

Cys Cys Asn Glu Met Asp Ile Leu Glu Ala Asn Ser Lys Ala Glu Ala
                195                 200                 205

Phe Thr Pro His Pro Cys Ile Gly Asp Asn Cys Asp Lys Gly Gly Cys
                210                 215                 220

Gly Phe Asn Pro Tyr Ala Leu Gly Gln Lys Ser Tyr Trp Gly Pro Gly
225                 230                 235                 240

Gly Thr Val Asp Thr Ser Lys Pro Phe Thr Ile Thr Gln Phe Ile
                245                 250                 255

Thr Asn Asp Gly Thr Thr Thr Gly Thr Leu Ser Glu Ile Arg Arg Gln
                260                 265                 270

Tyr Met Gln Asn Gly Lys Val Ile Ala Asn Ala Val Ser Ser Thr Gly
                275                 280                 285

Val Asn Ser Ile Thr Glu Asp Trp Cys Thr Ser Val Asp Gly Ser Ala
                290                 295                 300

Ala Thr Phe Gly Gly Leu Thr Thr Met Gly Lys Ala Leu Gly Arg Gly
305                 310                 315                 320

Met Val Leu Val Phe Ser Ile Trp Asn Asp Asn Ser Gln Tyr Met Asn
                325                 330                 335

Trp Leu Asp Ser Gly Asn Ala Gly Pro Cys Ser Ser Thr Glu Gly Asn
                340                 345                 350

Pro Ser Asn Ile Leu Ala Asn Asn Pro Asn Thr His Val Val Phe Ser
                355                 360                 365

Asn Ile Arg Trp Gly Asp Ile Gly Ser Thr Thr Asn Ser Thr Ala Pro
                370                 375                 380

Pro Pro Pro Pro Ala Ser Ser Thr Thr Phe Ser Thr Thr Arg Arg Ser
385                 390                 395                 400

Ser Thr Thr Ser Ser Ser Pro Ser Cys Thr Gln Thr His Trp Gly Gln
                405                 410                 415

Cys Gly Gly Ile Gly Tyr Ser Gly Cys Lys Thr Cys Thr Ser Gly Thr
                420                 425                 430

Thr Cys Gln Tyr Ser Asn Asp Tyr Tyr Ser Gln Cys Leu
                435                 440                 445

<210> SEQ ID NO 7
```

```
<211> LENGTH: 1131
<212> TYPE: DNA
<213> ORGANISM: Artificial Sequence
<220> FEATURE:
<223> OTHER INFORMATION: 107H12

<400> SEQUENCE: 7
cagcaaccgg gttcggtgac ccccgaggtc catcccaagt tgacaaccta caagtgtaca      60
aagtccgggg gtgcgtggc ccaggacacc tcggtggtcc ttgactgggg ctaccactgg      120
attcacacgg tcgatgggta cacatcgtgc accacatcgt ccggcgtcga cagcacgctc     180
tgccctgacg cggcgacctg tgcgaagaac tgcgtgatcg agccggccaa ctacaccagc     240
gccggcgtca cgacctcggg cgacagcctc accctgaggc agttcgtcaa ggacagcgag     300
ggcaagacca cagcgtctc tcctcgggcc tatctcctgg cgccgacgg tgactacgtg       360 atgttcaagc tcctcaacca ggagctgagc ttcgacgtcg acctctctac gctgccgtgt     420
ggagagaacg cagcgctcta cttctctgag atggacaaga ccgggggccg gaacgagcac     480
aacacgggcg gtgccaagta cgggagcggc tactgcgatg ctcagtgccc cgtccagaca     540
tggaacaacg gcaccctcaa cactagccac cagggctcgt gctgcaacga gatggatatc     600
ctggaggcca actcgaaggc ggaagccttc acccctcacc cctgcatcgg cgacaactgc     660
gacaagggcg gttgcggctt caactcgtat gcgcgcggca acaaaaacta ctgggcgccc     720
ggaggcaccc tcgacacctc caagcccttc accatggtga cccagttcat cacggacgac     780
ggcaccagct cgggcaagct tagccagatc gtgcgctcct acgtgcaaaa cggccagaag     840
gtcgccagcc ccgtgtccgg cggcgacagc atcaccgtcg agggctgctc gtcctccgac     900
gcctacggcg gcctcgtcgg tatgggcgag gccctgggcc gcggcatggt gctcgccatg     960
agcatttgga acgacgccag cggcttcatg aactggctcg acagcggcga caacggcccc    1020
tgcaacgaga ccgagggcga cccagccaac atcctggcca ccaccccga ttcgcaggtc     1080 gtcctgtcca acatccgctg gggagacatt gactctactg ttcagctcta a             1131

<210> SEQ ID NO 8
<211> LENGTH: 376
<212> TYPE: PRT
<213> ORGANISM: Artificial Sequence
<220> FEATURE:
<223> OTHER INFORMATION: 107H12

<400> SEQUENCE: 8

Gln Gln Pro Gly Ser Val Thr Pro Glu Val His Pro Lys Leu Thr Thr
1               5                  10                  15

Tyr Lys Cys Thr Lys Ser Gly Gly Cys Val Ala Gln Asp Thr Ser Val
            20                  25                  30

Val Leu Asp Trp Gly Tyr His Trp Ile His Thr Val Asp Gly Tyr Thr
        35                  40                  45

Ser Cys Thr Thr Ser Ser Gly Val Asp Ser Thr Leu Cys Pro Asp Ala
    50                  55                  60

Ala Thr Cys Ala Lys Asn Cys Val Ile Glu Pro Ala Asn Tyr Thr Ser
65                  70                  75                  80

Ala Gly Val Thr Thr Ser Gly Asp Ser Leu Thr Leu Arg Gln Phe Val
                85                  90                  95

Lys Asp Ser Glu Gly Lys Thr Asn Ser Val Ser Pro Arg Ala Tyr Leu
            100                 105                 110

Leu Gly Ala Asp Gly Asp Tyr Val Met Phe Lys Leu Leu Asn Gln Glu
        115                 120                 125
```

Leu Ser Phe Asp Val Asp Leu Ser Thr Leu Pro Cys Gly Glu Asn Ala
    130                 135                 140

Ala Leu Tyr Phe Ser Glu Met Asp Lys Thr Gly Gly Arg Asn Glu His
145                 150                 155                 160

Asn Thr Gly Gly Ala Lys Tyr Gly Ser Gly Tyr Cys Asp Ala Gln Cys
                165                 170                 175

Pro Val Gln Thr Trp Asn Asn Gly Thr Leu Asn Thr Ser His Gln Gly
            180                 185                 190

Ser Cys Cys Asn Glu Met Asp Ile Leu Glu Ala Asn Ser Lys Ala Glu
        195                 200                 205

Ala Phe Thr Pro His Pro Cys Ile Gly Asp Asn Cys Asp Lys Gly Gly
    210                 215                 220

Cys Gly Phe Asn Ser Tyr Ala Arg Gly Asn Lys Asn Tyr Trp Ala Pro
225                 230                 235                 240

Gly Gly Thr Leu Asp Thr Ser Lys Pro Phe Thr Met Val Thr Gln Phe
                245                 250                 255

Ile Thr Asp Asp Gly Thr Ser Ser Gly Lys Leu Ser Gln Ile Val Arg
            260                 265                 270

Ser Tyr Val Gln Asn Gly Gln Lys Val Ala Ser Ala Val Ser Gly Gly
        275                 280                 285

Asp Ser Ile Thr Val Glu Gly Cys Ser Ser Ser Asp Ala Tyr Gly Gly
    290                 295                 300

Leu Val Gly Met Gly Glu Ala Leu Gly Arg Gly Met Val Leu Ala Met
305                 310                 315                 320

Ser Ile Trp Asn Asp Ala Ser Gly Phe Met Asn Trp Leu Asp Ser Gly
                325                 330                 335

Asp Asn Gly Pro Cys Asn Glu Thr Glu Gly Asp Pro Ala Asn Ile Leu
            340                 345                 350

Ala Asn His Pro Asp Ser Gln Val Val Leu Ser Asn Ile Arg Trp Gly
        355                 360                 365

Asp Ile Asp Ser Thr Val Gln Leu
    370                 375

<210> SEQ ID NO 9
<211> LENGTH: 1320
<212> TYPE: DNA
<213> ORGANISM: Artificial Sequence
<220> FEATURE:
<223> OTHER INFORMATION: 154E4

<400> SEQUENCE: 9
cagcaaccgg gtaccagcac ccccgaggtc catcccaagt tgacaaccta caagtgtaca      60
actgctgggg ggtgcgtggc ccaggacacc tcggtggtcc ttgactgggg ctaccactgg     120
attcacacgg tcgatgggta cacatcgtgc accacatcgt ccggcgtcga cagcacgctc     180
tgccctgacg cggcgacctg tgcgaagaac tgcgtgatcg agccggccaa ctacaccagc     240
gccggcgtca cgacctcggg cgacagcctc accatgtacc agtacgttca gagcaacggc     300
gtctacacca cgcctctcc tcgggcctat ctcctgggcg ccgacggtga ctacgtgatg     360
ttcaagctcc tcaaccagga gctgagcttc gacgtcgacg tctctacgct gccgtgtgga     420
gagaacgcag cgctctactt ctctgagatg gacaagaccg ggggccggaa cgagcacaac     480
acgggcggtg ccaagtacgg gagcggctac tgcgatgctc agtgccccgt ccagacatgg     540
aacaacggca ccctcaacac tagccaccag ggctcgtgct gcaacgagat ggatatcctg     600

-continued

```
gaggccaact cgaaggcgga agccttcacc cctcacccct gcatcggcga caactgcgac    660
aagggcggtt gcggcttcaa ctcgtatgcg cgcggcaaca aaaactactg ggcgcccgga    720
ggcaccctcg acacctccaa gcccttcacc atggtgaccc agttcatcac ggacgacggc    780
accagctcgg gcaagcttag ccagatcgtg cgctcctacg tgcaaaacgg ccagaaggtc    840
gccagcgccg tgtccggcgg cgacagcatc accgtcgagg gctgctcgtc ctccgacgcc    900
tacggcggcc tcgtcggtat gggcgaggcc ctgggccgcg catggtgct cgtgttcagc     960
atttggaacg acaacagcca gtacatgaac tggctcgaca gcggcaacgc cggcccctgc    1020
agcagcaccg agggcaaccc atccaacatc ctggccaaca ccccaacac gcacgtcgtc     1080
ttctccaaca tccgctgggg agacattggg tctactacga actcgactgc gccccgccc    1140
ccgcctgcgt ccagcacgac gttttcgact cacggagga gctcgacgac ttcgagcagc    1200
ccgagctgca cgcagactca ctgggggcag tgcggtggca ttgggtacag cgggtgcaag    1260
acgtgcacgt cgggcactac gtgccagtat agcaacgact actactcgca atgcctttaa    1320
```

<210> SEQ ID NO 10
<211> LENGTH: 439
<212> TYPE: PRT
<213> ORGANISM: Artificial Sequence
<220> FEATURE:
<223> OTHER INFORMATION: 154E4

<400> SEQUENCE: 10

```
Gln Gln Pro Gly Thr Ser Thr Pro Glu Val His Pro Lys Leu Thr Thr
1               5                   10                  15

Tyr Lys Cys Thr Thr Ala Gly Gly Cys Val Ala Gln Asp Thr Ser Val
            20                  25                  30

Val Leu Asp Trp Gly Tyr His Trp Ile His Thr Val Asp Gly Tyr Thr
        35                  40                  45

Ser Cys Thr Thr Ser Ser Gly Val Asp Ser Thr Leu Cys Pro Asp Ala
    50                  55                  60

Ala Thr Cys Ala Lys Asn Cys Val Ile Glu Pro Ala Asn Tyr Thr Ser
65                  70                  75                  80

Ala Gly Val Thr Thr Ser Gly Asp Ser Leu Thr Met Tyr Gln Tyr Val
                85                  90                  95

Gln Ser Asn Gly Val Tyr Thr Asn Ala Ser Pro Arg Ala Tyr Leu Leu
            100                 105                 110

Gly Ala Asp Gly Asp Tyr Val Met Phe Lys Leu Leu Asn Gln Glu Leu
        115                 120                 125

Ser Phe Asp Val Asp Val Ser Thr Leu Pro Cys Gly Glu Asn Ala Ala
    130                 135                 140

Leu Tyr Phe Ser Glu Met Asp Lys Thr Gly Gly Arg Asn Glu His Asn
145                 150                 155                 160

Thr Gly Gly Ala Lys Tyr Gly Ser Gly Tyr Cys Asp Ala Gln Cys Pro
                165                 170                 175

Val Gln Thr Trp Asn Asn Gly Thr Leu Asn Thr Ser His Gln Gly Ser
            180                 185                 190

Cys Cys Asn Glu Met Asp Ile Leu Glu Ala Asn Ser Lys Ala Glu Ala
        195                 200                 205

Phe Thr Pro His Pro Cys Ile Gly Asp Asn Cys Asp Lys Gly Gly Cys
    210                 215                 220

Gly Phe Asn Ser Tyr Ala Arg Gly Asn Lys Asn Tyr Trp Ala Pro Gly
225                 230                 235                 240
```

Gly Thr Leu Asp Thr Ser Lys Pro Phe Thr Met Val Thr Gln Phe Ile
            245                 250                 255

Thr Asp Asp Gly Thr Ser Ser Gly Lys Leu Ser Gln Ile Val Arg Ser
        260                 265                 270

Tyr Val Gln Asn Gly Gln Lys Val Ala Ser Ala Val Ser Gly Gly Asp
    275                 280                 285

Ser Ile Thr Val Glu Gly Cys Ser Ser Asp Ala Tyr Gly Gly Leu
    290                 295                 300

Val Gly Met Gly Glu Ala Leu Gly Arg Gly Met Val Leu Val Phe Ser
305                 310                 315                 320

Ile Trp Asn Asp Asn Ser Gln Tyr Met Asn Trp Leu Asp Ser Gly Asn
                325                 330                 335

Ala Gly Pro Cys Ser Ser Thr Glu Gly Asn Pro Ser Asn Ile Leu Ala
            340                 345                 350

Asn Asn Pro Asn Thr His Val Phe Ser Asn Ile Arg Trp Gly Asp
        355                 360                 365

Ile Gly Ser Thr Thr Asn Ser Thr Ala Pro Pro Pro Pro Ala Ser
    370                 375                 380

Ser Thr Thr Phe Ser Thr Thr Arg Arg Ser Ser Thr Thr Ser Ser Ser
385                 390                 395                 400

Pro Ser Cys Thr Gln Thr His Trp Gly Gln Cys Gly Gly Ile Gly Tyr
                405                 410                 415

Ser Gly Cys Lys Thr Cys Thr Ser Gly Thr Thr Cys Gln Tyr Ser Asn
            420                 425                 430

Asp Tyr Tyr Ser Gln Cys Leu
        435

<210> SEQ ID NO 11
<211> LENGTH: 1320
<212> TYPE: DNA
<213> ORGANISM: Artificial Sequence
<220> FEATURE:
<223> OTHER INFORMATION: 202C12

<400> SEQUENCE: 11
cagcaaccgg gtaccagcac ccccgaggtc catcccaagt tgacaaccta caagtgtaca      60
aagtccgggg ggtgcgtggc ccaggacacc tcggtggtcc ttgactggaa ctaccgctgg     120
atgcacgacg caaactacaa ctcgtgcacc gtcaacggcg cgtcaacac acgtctctgc     180 cctgacgagg cgacctgtgg caagaactgc ttcatcgagg cgtcgacta cgccgcctcg     240 ggcgtcacga cctcgggcag cagcctcacc ctgaggcagt cgtcaagga cagcgagggc     300 aagaccaaca gcgtctctcc tcgggcctat ctcctgggcg ccgacggtga ctacgtgatg     360
ttcaagctcc tcaaccagga gctgagcttc gacgtcgacg tctctacgct gccgtgtgga     420
gagaacgcag cgctctactt ctctgagatg gacaagaccg ggggccggaa cgagcacaac     480
acgggcggtg ccgagtacgg gagcggctac tgcgatgctc agtgccccgt ccagacatgg     540
aacaacggca ccctcaacac tagccaccag ggctcgtgct gcaacgagat ggatatcctg     600
gaggccaact cgaaggcgga agccttcacc cctcacccct gcatcggcga caactgcgac     660
aagggcggtt gcggcttcaa ctcgtatcgc cgcggcaaca aaaactactg ggcgcccgga     720 ggcacccteg acacctccaa gcccttcacc atggtgaccc agttcatcac ggacgacggc     780
accagctcgg gcaagcttag ccagatcgtg cgctcctacg tgcaaaacgg ccagaaggtc     840
gccagcgccg tgtccggcgg cgacagcatc accgtcgagg gctgctcgtc ctccgacgcc     900

```
tacggcggcc tcgtcggtat gggcgaggcc ctgggccgcg gcatggtgct cgccatgagc    960
atttggaacg acgccagcgg cttcatgaac tggctcgaca cggcgacaa cggcccctgc   1020 aacgagaccg agggcaaccc atccaacatc ctggccaaca accccaacac gcacgtcgtc   1080
ttctccaaca tccgctgggg agacattggg tctactacga actcgactgc cccccgccc   1140 ccgcctgcgt ccagcacgac gttttcgact acacggagga gctcgacgac ttcgagcagc   1200
ccgagctgca cgcagactca ctgggggcag tgcggtggca ttgggtacag cgggtgcaag   1260
acgtgcacgt cgggcactac gtgccagtat agcaacgact actactcgca atgcctttaa   1320
```

<210> SEQ ID NO 12
<211> LENGTH: 439
<212> TYPE: PRT
<213> ORGANISM: Artificial Sequence
<220> FEATURE:
<223> OTHER INFORMATION: 202C12

<400> SEQUENCE: 12

```
Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
                20                  25                  30

Val Leu Asp Trp Asn Tyr Arg Trp Met His Asp Ala Asn Tyr Asn Ser
            35                  40                  45

Cys Thr Val Asn Gly Gly Val Asn Thr Thr Leu Cys Pro Asp Glu Ala
        50                  55                  60

Thr Cys Gly Lys Asn Cys Phe Ile Glu Gly Val Asp Tyr Ala Ala Ser
65                  70                  75                  80

Gly Val Thr Thr Ser Gly Ser Ser Leu Thr Leu Arg Gln Phe Val Lys
                85                  90                  95

Asp Ser Glu Gly Lys Thr Asn Ser Val Ser Pro Arg Ala Tyr Leu Leu
                100                 105                 110

Gly Ala Asp Gly Asp Tyr Val Met Phe Lys Leu Leu Asn Gln Glu Leu
            115                 120                 125

Ser Phe Asp Val Asp Val Ser Thr Leu Pro Cys Gly Glu Asn Ala Ala
130                 135                 140

Leu Tyr Phe Ser Glu Met Asp Lys Thr Gly Gly Arg Asn Glu His Asn
145                 150                 155                 160

Thr Gly Gly Ala Glu Tyr Gly Ser Gly Tyr Cys Asp Ala Gln Cys Pro
                165                 170                 175

Val Gln Thr Trp Asn Asn Gly Thr Leu Asn Thr Ser His Gln Gly Ser
            180                 185                 190

Cys Cys Asn Glu Met Asp Ile Leu Glu Ala Asn Ser Lys Ala Glu Ala
        195                 200                 205

Phe Thr Pro His Pro Cys Ile Gly Asp Asn Cys Asp Lys Gly Gly Cys
    210                 215                 220

Gly Phe Asn Ser Tyr Ala Arg Gly Asn Lys Asn Tyr Trp Ala Pro Gly
225                 230                 235                 240

Gly Thr Leu Asp Thr Ser Lys Pro Phe Thr Met Val Thr Gln Phe Ile
                245                 250                 255

Thr Asp Asp Gly Thr Ser Ser Gly Lys Leu Ser Gln Ile Val Arg Ser
            260                 265                 270

Tyr Val Gln Asn Gly Gln Lys Val Ala Ser Ala Val Ser Gly Gly Asp
        275                 280                 285

Ser Ile Thr Val Glu Gly Cys Ser Ser Ser Asp Ala Tyr Gly Gly Leu
```

```
            290                 295                 300
Val Gly Met Gly Glu Ala Leu Gly Arg Gly Met Val Leu Ala Met Ser
305                 310                 315                 320

Ile Trp Asn Asp Ala Ser Gly Phe Met Asn Trp Leu Asp Ser Gly Asp
                325                 330                 335

Asn Gly Pro Cys Asn Glu Thr Glu Gly Asn Pro Ser Asn Ile Leu Ala
            340                 345                 350

Asn Asn Pro Asn Thr His Val Val Phe Ser Asn Ile Arg Trp Gly Asp
        355                 360                 365

Ile Gly Ser Thr Thr Asn Ser Thr Ala Pro Pro Pro Pro Ala Ser
    370                 375                 380

Ser Thr Thr Phe Ser Thr Thr Arg Arg Ser Ser Thr Thr Ser Ser Ser
385                 390                 395                 400

Pro Ser Cys Thr Gln Thr His Trp Gly Gln Cys Gly Gly Ile Gly Tyr
                405                 410                 415

Ser Gly Cys Lys Thr Cys Thr Ser Gly Thr Thr Cys Gln Tyr Ser Asn
            420                 425                 430

Asp Tyr Tyr Ser Gln Cys Leu
        435
```

<210> SEQ ID NO 13
<211> LENGTH: 1323
<212> TYPE: DNA
<213> ORGANISM: Artificial Sequence
<220> FEATURE:
<223> OTHER INFORMATION: 272A9

<400> SEQUENCE: 13

```
cagcaaccgg gtaccagcac ccccgaggtc catcccaagt tgacaaccta caagtgtaca      60
aagtccgggg ggtgcgtggc caggacacct cggtggtcc ttgactggaa ctaccgctgg     120
atgcacgacg caaactacaa ctcgtgcacc gtcaacggcg cgtcaacac cacgctctgc     180
cctgacgcgg cgacctgtgc gaagaactgc gtgatcgagc cggccaacta caccagcgcc     240
ggcgtcacga cctcgggcga cagcctcacc atgtaccagt acgttcagag caacggcgtc     300
tacaccaacg cctctcctcg gctgtatctc ctgggccccg acaagaacta cgtgatgctg     360
aagctcctag gccaggagct gagcttcgac gtcgacctct ctgctctgcc gtgtggagag     420
aacggcgccc tctacctgtc tgaaatgagc gccaccgggg ccgcaacga atataacacg     480
ggcggtgccg agtacgggag cggctactgc gatgctcagt gccccgtcat cgcctggaag     540
aacggcaccc tcaacactag cggcgcaagc tactgctgca cgagatgga tatcctggag     600
gccaactcga gggcgaattc gtacacccct caccccctgca gtgccacgga ctgcgacaag     660
ggcggttgcg gcttcaaccc ctatgctctc ggccaaaaaa gctactgggg ccccggaggc     720
accgttgaca cctccaagcc cttcaccatc accacccagt tcatcacgaa cgacggcacc     780
accaccggca ccctttccga aatccgccgc cagtacatgc aaaacggcaa ggtgatcgcc     840
aatgccgttt cctccactgg cgtcaactcc atcaccgagg actggtgcac gtccgtcgac     900
ggctcggccg ccacctttgg cggcctcacc accatgggca aggccctggg ccgcggcatg     960
gtgctcatct tcagcatttg aacgacgcc agcggcttta tgaactggct cgacagcggc    1020
aacgccggcc cctgcagcag caccgagggc aacccagact tgatcaaggc ccagaacccc    1080
acgacgcacg tcgtcttctc caacatccgc tggggagaca ttgggtctac tttcaagggt    1140
tctgatggct cggtgacgac gacgacgtcg actacatcga ccaagaccac gacttcgacc    1200
```

```
gcgccggggc aacgcagac tcactatggg cagtgcggtg gccaagggtg gactgggccc    1260
acggcttgcg catcgcccta cacgtgccag gttctgaacc cgtggtactc gcaatgcctt    1320
taa                                                                  1323
```

<210> SEQ ID NO 14
<211> LENGTH: 440
<212> TYPE: PRT
<213> ORGANISM: Artificial Sequence
<220> FEATURE:
<223> OTHER INFORMATION: 272A9

<400> SEQUENCE: 14

```
Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
            20                  25                  30

Val Leu Asp Trp Asn Tyr Arg Trp Met His Asp Ala Asn Tyr Asn Ser
        35                  40                  45

Cys Thr Val Asn Gly Gly Val Asn Thr Thr Leu Cys Pro Asp Ala Ala
    50                  55                  60

Thr Cys Ala Lys Asn Cys Val Ile Glu Pro Ala Asn Tyr Thr Ser Ala
65                  70                  75                  80

Gly Val Thr Thr Ser Gly Asp Ser Leu Thr Met Tyr Gln Tyr Val Gln
                85                  90                  95

Ser Asn Gly Val Tyr Thr Asn Ala Ser Pro Arg Leu Tyr Leu Leu Gly
            100                 105                 110

Pro Asp Lys Asn Tyr Val Met Leu Lys Leu Leu Gly Gln Glu Leu Ser
        115                 120                 125

Phe Asp Val Asp Leu Ser Ala Leu Pro Cys Gly Glu Asn Gly Ala Leu
    130                 135                 140

Tyr Leu Ser Glu Met Ser Ala Thr Gly Gly Arg Asn Glu Tyr Asn Thr
145                 150                 155                 160

Gly Gly Ala Glu Tyr Gly Ser Gly Tyr Cys Asp Ala Gln Cys Pro Val
                165                 170                 175

Ile Ala Trp Lys Asn Gly Thr Leu Asn Thr Ser Gly Ala Ser Tyr Cys
            180                 185                 190

Cys Asn Glu Met Asp Ile Leu Glu Ala Asn Ser Arg Ala Asn Ser Tyr
        195                 200                 205

Thr Pro His Pro Cys Ser Ala Thr Asp Cys Asp Lys Gly Gly Cys Gly
    210                 215                 220

Phe Asn Pro Tyr Ala Leu Gly Gln Lys Ser Tyr Trp Gly Pro Gly Gly
225                 230                 235                 240

Thr Val Asp Thr Ser Lys Pro Phe Thr Ile Thr Thr Gln Phe Ile Thr
                245                 250                 255

Asn Asp Gly Thr Thr Thr Gly Thr Leu Ser Glu Ile Arg Arg Gln Tyr
            260                 265                 270

Met Gln Asn Gly Lys Val Ile Ala Asn Ala Val Ser Thr Gly Val
        275                 280                 285

Asn Ser Ile Thr Glu Asp Trp Cys Thr Ser Val Asp Gly Ser Ala Ala
    290                 295                 300

Thr Phe Gly Gly Leu Thr Thr Met Gly Lys Ala Leu Gly Arg Gly Met
305                 310                 315                 320

Val Leu Ile Phe Ser Ile Trp Asn Asp Ala Ser Gly Phe Met Asn Trp
                325                 330                 335
```

-continued

Leu Asp Ser Gly Asn Ala Gly Pro Cys Ser Ser Thr Glu Gly Asn Pro
            340                 345                 350

Asp Leu Ile Lys Ala Gln Asn Pro Thr Thr His Val Val Phe Ser Asn
        355                 360                 365

Ile Arg Trp Gly Asp Ile Gly Ser Thr Phe Lys Gly Ser Asp Gly Ser
370                 375                 380

Val Thr Thr Thr Thr Ser Thr Thr Ser Thr Lys Thr Thr Thr Ser Thr
385                 390                 395                 400

Ala Pro Gly Pro Thr Gln Thr His Tyr Gly Gln Cys Gly Gly Gln Gly
                405                 410                 415

Trp Thr Gly Pro Thr Ala Cys Ala Ser Pro Tyr Thr Cys Gln Val Leu
            420                 425                 430

Asn Pro Trp Tyr Ser Gln Cys Leu
        435                 440

<210> SEQ ID NO 15
<211> LENGTH: 1317
<212> TYPE: DNA
<213> ORGANISM: Artificial Sequence
<220> FEATURE:
<223> OTHER INFORMATION: 278F10

<400> SEQUENCE: 15
cagcaaccgg gtaccagcac ccccgaggtc catcccaagt tgacaaccta caagtgtaca      60
aagtccgggg ggtgcgtgga gcaggacacc tcggtggtcc ttgactggaa ctaccgctgg     120
ttccacacct cggacaacac cacctcgtgc accacgtcct cgggcatcga ctcgacgctc     180
tgccctgacg cagcgacctg tgccgagaac tgcgtcgtgg agggcaccga ctacaccagc     240
tcgggcatcg agacctcggg cagcagcctc accctgaggc agttcgtcaa ggacagcgag     300
ggcaagacca acagcgtctc tcctcgggcc tatctcctgg gcgccgacgg tgactacgtg     360
atgttcaagc tcctcaacca ggagctgagc ttcgacgtcg acgtctctac gctgccgtgt     420
ggagagaacg cagcgctcta cttctctgag atggacaaga ccggggggccg gaacgagcac     480 aacacgggcg gtgccaagta cgggagcggc tactgcgatg ctcagtgccc cgtccagaca     540
tggaacaacg gcaccctcaa cactagccac cagggctcgt gctgcaacga gatggatatc     600
ctggaggcca actcgaaggc ggaagccttc accctcacc cctgcatcgg cgacaactgc     660
gacaagggcg gttgcggctt caactcgtat gcgcgcggca caaaaaacta ctgggcgccc     720
ggaggcaccc tcgacacctc caagcccttc accatggtga cccagttcat cacggacgac     780
ggcaccagct cgggcaacct tgtgagcatc acccgcaagt accagcaaaa cggcgtcgac     840
atccccagcg cccagcccgg cggcgacacc atctcgtcct gcccgtccgc ctcagcctac     900
ggcggcctcg ccaccatggg caaggccctg agcagcggca tggtgctcgt gttcagcatt     960
tggaacgaca cagccagta catgaactgg ctcgacagcg gcaacgccgg ccctgcagc    1020 agcaccgagg gcaacccatc caacatcctg ccaacaacc caacacgca cgtcgtcttc    1080 tccaacatcc gctggggaga cattgggtct actacgaact cgactgcgcc ccgcccccg    1140 cctgcgtcca gcacgacgtt ttcgactaca cggaggagct cgacgacttc gagcagcccg    1200
agctgcacgc agactcactg ggggcagtgc ggtggcattg gtacagcgg gtgcaagacg    1260 tgcacgtcgg gcactacgtg ccagtatagc aacgactact actcgcaatg cctttaa      1317

<210> SEQ ID NO 16
<211> LENGTH: 438
<212> TYPE: PRT

<213> ORGANISM: Artificial Sequence
<220> FEATURE:
<223> OTHER INFORMATION: 278F10

<400> SEQUENCE: 16

| | | | | | | | | | | | | | | |
|---|---|---|---|---|---|---|---|---|---|---|---|---|---|---|
| Gln | Gln | Pro | Gly | Thr | Ser | Thr | Pro | Glu | Val | His | Pro | Lys | Leu | Thr | Thr |
| 1 | | | | 5 | | | | | 10 | | | | | 15 | |
| Tyr | Lys | Cys | Thr | Lys | Ser | Gly | Gly | Cys | Val | Glu | Gln | Asp | Thr | Ser | Val |
| | | | 20 | | | | | 25 | | | | | 30 | | |
| Val | Leu | Asp | Trp | Asn | Tyr | Arg | Trp | Phe | His | Thr | Ser | Asp | Asn | Thr | Thr |
| | | 35 | | | | | 40 | | | | | 45 | | | |
| Ser | Cys | Thr | Thr | Ser | Ser | Gly | Ile | Asp | Ser | Thr | Leu | Cys | Pro | Asp | Ala |
| 50 | | | | | 55 | | | | | 60 | | | | | |
| Ala | Thr | Cys | Ala | Glu | Asn | Cys | Val | Val | Glu | Gly | Thr | Asp | Tyr | Thr | Ser |
| 65 | | | | 70 | | | | | 75 | | | | | 80 | |
| Ser | Gly | Ile | Glu | Thr | Ser | Gly | Ser | Ser | Leu | Thr | Leu | Arg | Gln | Phe | Val |
| | | | | 85 | | | | | 90 | | | | | 95 | |
| Lys | Asp | Ser | Glu | Gly | Lys | Thr | Asn | Ser | Val | Ser | Pro | Arg | Ala | Tyr | Leu |
| | | | 100 | | | | | 105 | | | | | 110 | | |
| Leu | Gly | Ala | Asp | Gly | Asp | Tyr | Val | Met | Phe | Lys | Leu | Leu | Asn | Gln | Glu |
| | | 115 | | | | | 120 | | | | | 125 | | | |
| Leu | Ser | Phe | Asp | Val | Asp | Val | Ser | Thr | Leu | Pro | Cys | Gly | Glu | Asn | Ala |
| | 130 | | | | | 135 | | | | | 140 | | | | |
| Ala | Leu | Tyr | Phe | Ser | Glu | Met | Asp | Lys | Thr | Gly | Gly | Arg | Asn | Glu | His |
| 145 | | | | | 150 | | | | | 155 | | | | | 160 |
| Asn | Thr | Gly | Gly | Ala | Lys | Tyr | Gly | Ser | Gly | Tyr | Cys | Asp | Ala | Gln | Cys |
| | | | | 165 | | | | | 170 | | | | | 175 | |
| Pro | Val | Gln | Thr | Trp | Asn | Asn | Gly | Thr | Leu | Asn | Thr | Ser | His | Gln | Gly |
| | | | 180 | | | | | 185 | | | | | 190 | | |
| Ser | Cys | Cys | Asn | Glu | Met | Asp | Ile | Leu | Glu | Ala | Asn | Ser | Lys | Ala | Glu |
| | | 195 | | | | | 200 | | | | | 205 | | | |
| Ala | Phe | Thr | Pro | His | Pro | Cys | Ile | Gly | Asp | Asn | Cys | Asp | Lys | Gly | Gly |
| | 210 | | | | | 215 | | | | | 220 | | | | |
| Cys | Gly | Phe | Asn | Ser | Tyr | Ala | Arg | Gly | Asn | Lys | Asn | Tyr | Trp | Ala | Pro |
| 225 | | | | | 230 | | | | | 235 | | | | | 240 |
| Gly | Gly | Thr | Leu | Asp | Thr | Ser | Lys | Pro | Phe | Thr | Met | Val | Thr | Gln | Phe |
| | | | 245 | | | | | 250 | | | | | 255 | | |
| Ile | Thr | Asp | Asp | Gly | Thr | Ser | Ser | Gly | Asn | Leu | Val | Ser | Ile | Thr | Arg |
| | | | 260 | | | | | 265 | | | | | 270 | | |
| Lys | Tyr | Gln | Gln | Asn | Gly | Val | Asp | Ile | Pro | Ser | Ala | Gln | Pro | Gly | Gly |
| | | 275 | | | | | 280 | | | | | 285 | | | |
| Asp | Thr | Ile | Ser | Ser | Cys | Pro | Ser | Ala | Ser | Ala | Tyr | Gly | Gly | Leu | Ala |
| | 290 | | | | | 295 | | | | | 300 | | | | |
| Thr | Met | Gly | Lys | Ala | Leu | Ser | Ser | Gly | Met | Val | Leu | Val | Phe | Ser | Ile |
| 305 | | | | | 310 | | | | | 315 | | | | | 320 |
| Trp | Asn | Asp | Asn | Ser | Gln | Tyr | Met | Asn | Trp | Leu | Asp | Ser | Gly | Asn | Ala |
| | | | | 325 | | | | | 330 | | | | | 335 | |
| Gly | Pro | Cys | Ser | Ser | Thr | Glu | Gly | Asn | Pro | Ser | Asn | Ile | Leu | Ala | Asn |
| | | | 340 | | | | | 345 | | | | | 350 | | |
| Asn | Pro | Asn | Thr | His | Val | Val | Phe | Ser | Asn | Ile | Arg | Trp | Gly | Asp | Ile |
| | | 355 | | | | | 360 | | | | | 365 | | | |
| Gly | Ser | Thr | Thr | Asn | Ser | Thr | Ala | Pro | Pro | Pro | Pro | Pro | Ala | Ser | Ser |
| | 370 | | | | | 375 | | | | | 380 | | | | |
| Thr | Thr | Phe | Ser | Thr | Thr | Arg | Arg | Ser | Ser | Thr | Thr | Ser | Ser | Ser | Pro |

```
            385                 390                 395                 400
Ser Cys Thr Gln Thr His Trp Gly Gln Cys Gly Gly Ile Gly Tyr Ser
                405                 410                 415

Gly Cys Lys Thr Cys Thr Ser Gly Thr Thr Cys Gln Tyr Ser Asn Asp
                420                 425                 430

Tyr Tyr Ser Gln Cys Leu
            435

<210> SEQ ID NO 17
<211> LENGTH: 1323
<212> TYPE: DNA
<213> ORGANISM: Artificial Sequence
<220> FEATURE:
<223> OTHER INFORMATION: 293B2

<400> SEQUENCE: 17
cagcaaccgg gttcggtgac ccccgaggtc catcccaagt tgcccacctg gcagtgtaca      60
aagtccgggg ggtgcgtgga gcaggacacc tcggtggtcc ttgactggaa ctaccgctgg     120
ttccacacct cggacaacac cacctcgtgc accacgtcct cgggcatcga ctcgacgctc     180
tgccctgacg cagcgacctg tgccgagaac tgcgtcgtgg agggcaccga ctacaccagc     240
tcgggcatcg agacctcggg cagcagcctc accctgaggc agttcgtcaa ggacagcgag     300
ggcaagacca cagcgtctc tcctcgggcc tatctcctgg cgccgacgg tgactacgtg       360 atgttcaagc tcctcaacca ggagctgagc ttcgacgtcg acgtctctac gctgccgtgt     420
ggagagaacg cagcgctcta cttctctgag atggacaaga ccgggggccg gaacgagcac     480
aacacgggcg gtgccaagta cgggagcggc tactgcgatg ctcagtgccc cgtccagaca     540
tggaacaacg gcacccctcaa cactagccac cagggctcgt gctgcaacga gatggatatc    600
ctggaggcca actcgaaggc ggaagccttc acccctcacc cctgcatcgg cgacaactgc    660
gacaagggcg gttgcggctt caactcgtat gcgcgcggca acaaaaacta ctgggcgccc    720
ggaggcaccc tcgacacctc caagcccttc accatggtga cccagttcat cacggacgac    780
ggcaccagct cgggcaagct tagccagatc gtgcgctcct acgtgcaaaa cggccagaag    840
gtcgccagcg ccgtgtccgg cggcgacagc atcaccgtcg agggctgctc gtcctccgac    900
gcctacggcg cctcgtcgg tatgggcgag gccctgggcc gcggcatggt gctcgtgttc    960
agcatttgga cgacaacag ccagtacatg aactggctcg acagcggcaa cgccggcccc    1020
tgcagcagca ccgagggcaa cccatccaac atcctggcca caacccaca cacgcacgtc    1080 gtcttctcca acatccgctg gggagacatt gggtctacta cgaactcgac tgcgcccccg    1140
cccccgcctg cgtccagcac gacgttttcg actacacgga ggagctcgac gacttcgagc    1200
agcccgagct gcacgcagac tcactggggg cagtgcggtg cattgggta cagcgggtgc    1260 aagacgtgca cgtcgggcac tacgtgccag tatagcaacg actactactc gcaatgcctt    1320
taa                                                                 1323

<210> SEQ ID NO 18
<211> LENGTH: 440
<212> TYPE: PRT
<213> ORGANISM: Artificial Sequence
<220> FEATURE:
<223> OTHER INFORMATION: 293B2

<400> SEQUENCE: 18

Gln Gln Pro Gly Ser Val Thr Pro Glu Val His Pro Lys Leu Pro Thr
1               5                   10                  15
```

```
Trp Gln Cys Thr Lys Ser Gly Gly Cys Val Glu Gln Asp Thr Ser Val
            20              25              30

Val Leu Asp Trp Asn Tyr Arg Trp Phe His Thr Ser Asp Asn Thr Thr
        35              40              45

Ser Cys Thr Thr Ser Ser Gly Ile Asp Ser Thr Leu Cys Pro Asp Ala
    50              55              60

Ala Thr Cys Ala Glu Asn Cys Val Val Glu Gly Thr Asp Tyr Thr Ser
65              70              75              80

Ser Gly Ile Glu Thr Ser Gly Ser Ser Leu Thr Leu Arg Gln Phe Val
            85              90              95

Lys Asp Ser Glu Gly Lys Thr Asn Ser Val Ser Pro Arg Ala Tyr Leu
        100             105             110

Leu Gly Ala Asp Gly Asp Tyr Val Met Phe Lys Leu Leu Asn Gln Glu
    115             120             125

Leu Ser Phe Asp Val Asp Val Ser Thr Leu Pro Cys Gly Glu Asn Ala
130             135             140

Ala Leu Tyr Phe Ser Glu Met Asp Lys Thr Gly Gly Arg Asn Glu His
145             150             155             160

Asn Thr Gly Gly Ala Lys Tyr Gly Ser Gly Tyr Cys Asp Ala Gln Cys
            165             170             175

Pro Val Gln Thr Trp Asn Asn Gly Thr Leu Asn Thr Ser His Gln Gly
        180             185             190

Ser Cys Cys Asn Glu Met Asp Ile Leu Glu Ala Asn Ser Lys Ala Glu
    195             200             205

Ala Phe Thr Pro His Pro Cys Ile Gly Asp Asn Cys Asp Lys Gly Gly
210             215             220

Cys Gly Phe Asn Ser Tyr Ala Arg Gly Asn Lys Asn Tyr Trp Ala Pro
225             230             235             240

Gly Gly Thr Leu Asp Thr Ser Lys Pro Phe Thr Met Val Thr Gln Phe
            245             250             255

Ile Thr Asp Asp Gly Thr Ser Ser Gly Lys Leu Ser Gln Ile Val Arg
        260             265             270

Ser Tyr Val Gln Asn Gly Gln Lys Val Ala Ser Ala Val Ser Gly Gly
    275             280             285

Asp Ser Ile Thr Val Glu Gly Cys Ser Ser Asp Ala Tyr Gly Gly
290             295             300

Leu Val Gly Met Gly Glu Ala Leu Gly Arg Gly Met Val Leu Val Phe
305             310             315             320

Ser Ile Trp Asn Asp Asn Ser Gln Tyr Met Asn Trp Leu Asp Ser Gly
            325             330             335

Asn Ala Gly Pro Cys Ser Ser Thr Glu Gly Asn Pro Ser Asn Ile Leu
        340             345             350

Ala Asn Asn Pro Asn Thr His Val Val Phe Ser Asn Ile Arg Trp Gly
    355             360             365

Asp Ile Gly Ser Thr Thr Asn Ser Thr Ala Pro Pro Pro Pro Ala
370             375             380

Ser Ser Thr Thr Phe Ser Thr Thr Arg Arg Ser Ser Thr Thr Ser Ser
385             390             395             400

Ser Pro Ser Cys Thr Gln Thr His Trp Gly Gln Cys Gly Gly Ile Gly
            405             410             415

Tyr Ser Gly Cys Lys Thr Cys Thr Ser Gly Thr Thr Cys Gln Tyr Ser
        420             425             430
```

Asn Asp Tyr Tyr Ser Gln Cys Leu
         435                 440

<210> SEQ ID NO 19
<211> LENGTH: 1323
<212> TYPE: DNA
<213> ORGANISM: Artificial Sequence
<220> FEATURE:
<223> OTHER INFORMATION: 309A11

<400> SEQUENCE: 19

| | | | | |
|---|---|---|---|---|
| cagcaaccgg gttcggtgac ccccgaggtc catcccaagt tgcccacctg gcagtgtaca | 60 |
| aagtccgggg ggtgcgtgga gcaggacacc tcggtggtcc ttgactggaa ctaccgctgg | 120 |
| ttccacacct cggacaacac cacctcgtgc accacgtcct cgggcatcga ctcgacgctc | 180 |
| tgccctgacg cagcgacctg tgccgagaac tgcgtcgtgg agggcaccga ctacaccagc | 240 |
| tcgggcatcg agacctcggg cagcagcctc accctgaggc agttcgtcaa ggacagcgag | 300 |
| ggcaagacca cagcgtctc tcctcgggcc tatctcctgg gcgccgacgg tgactacgtg | 360 |
| atgttcaagc tcctcaacca ggagctgagc ttcgacgtcg acgtctctac gctgccgtgt | 420 |
| ggagagaacg cagcgctcta cttctctgag atggacaaga ccgggggccg gaacgagcac | 480 |
| aacacgggcg gtgccaagta cgggagcggc tactgcgatg ctcagtgccc cgtccagaca | 540 |
| tggaacaacg gcaccctcaa cactagccac cagggctcgt gctgcaacga gatggatatc | 600 |
| ctggaggcca actcgaaggc ggaagccttc accctcacc cctgcatcgg cgacaactgc | 660 |
| gacaagggcg gttgcggctt caactcgtat gcgcgcggca caaaaaacta ctgggcgccc | 720 |
| ggaggcaccc tcgacacctc caagcccttc accatggtga cccagttcat cacggacgac | 780 |
| ggcaccagct cgggcaagct tagccagatc gtgcgctcct acgtgcaaaa cggccagaag | 840 |
| gtcgccagcg ccgtgtccgg cggcgacagc atcaccgtcg agggctgctc gtccgcctca | 900 |
| gcctacggcg gcctcgccac catgggcaag gccctgagca gcggcatggt gctcgtgttc | 960 |
| agcatttgga acgacaacag ccagtacatg aactggctcg acagcggcaa cgccggcccc | 1020 |
| tgcagcagca ccgagggcaa cccatccaac atcctggcca caacccccaa cacgcacgtc | 1080 |
| gtcttctcca acatccgctg gggagacatt gggtctacta cgaactcgac tgcgcccccg | 1140 |
| ccccccgcctg cgtccagcac gacgtttcg actacacgga ggagctcgac gacttcgagc | 1200 |
| agcccgagct gcacgcagac tcactggggg cagtgcggtg gcattgggta cagcgggtgc | 1260 |
| aagacgtgca cgtcgggcac tacgtgccag tatagcaacg actactactc gcaatgcctt | 1320 |
| taa | 1323 |

<210> SEQ ID NO 20
<211> LENGTH: 440
<212> TYPE: PRT
<213> ORGANISM: Artificial Sequence
<220> FEATURE:
<223> OTHER INFORMATION: 309A1

<400> SEQUENCE: 20

Gln Gln Pro Gly Ser Val Thr Pro Glu Val His Pro Lys Leu Pro Thr
1               5                   10                  15

Trp Gln Cys Thr Lys Ser Gly Gly Cys Val Glu Gln Asp Thr Ser Val
            20                  25                  30

Val Leu Asp Trp Asn Tyr Arg Trp Phe His Thr Ser Asp Asn Thr Thr
        35                  40                  45

Ser Cys Thr Thr Ser Ser Gly Ile Asp Ser Thr Leu Cys Pro Asp Ala

```
                 50                  55                  60
Ala Thr Cys Ala Glu Asn Cys Val Val Glu Gly Thr Asp Tyr Thr Ser
 65                  70                  75                  80

Ser Gly Ile Glu Thr Ser Gly Ser Ser Leu Thr Leu Arg Gln Phe Val
                     85                  90                  95

Lys Asp Ser Glu Gly Lys Thr Asn Ser Val Ser Pro Arg Ala Tyr Leu
                    100                 105                 110

Leu Gly Ala Asp Gly Asp Tyr Val Met Phe Lys Leu Leu Asn Gln Glu
                    115                 120                 125

Leu Ser Phe Asp Val Asp Val Ser Thr Leu Pro Cys Gly Glu Asn Ala
                    130                 135                 140

Ala Leu Tyr Phe Ser Glu Met Asp Lys Thr Gly Gly Arg Asn Glu His
145                 150                 155                 160

Asn Thr Gly Gly Ala Lys Tyr Gly Ser Gly Tyr Cys Asp Ala Gln Cys
                    165                 170                 175

Pro Val Gln Thr Trp Asn Asn Gly Thr Leu Asn Thr Ser His Gln Gly
                    180                 185                 190

Ser Cys Cys Asn Glu Met Asp Ile Leu Glu Ala Asn Ser Lys Ala Glu
                    195                 200                 205

Ala Phe Thr Pro His Pro Cys Ile Gly Asp Asn Cys Asp Lys Gly Gly
                    210                 215                 220

Cys Gly Phe Asn Ser Tyr Ala Arg Gly Asn Lys Asn Tyr Trp Ala Pro
225                 230                 235                 240

Gly Gly Thr Leu Asp Thr Ser Lys Pro Phe Thr Met Val Thr Gln Phe
                    245                 250                 255

Ile Thr Asp Asp Gly Thr Ser Ser Gly Lys Leu Ser Gln Ile Val Arg
                    260                 265                 270

Ser Tyr Val Gln Asn Gly Gln Lys Val Ala Ser Ala Val Ser Gly Gly
                    275                 280                 285

Asp Ser Ile Thr Val Glu Gly Cys Ser Ser Ala Ser Ala Tyr Gly Gly
                    290                 295                 300

Leu Ala Thr Met Gly Lys Ala Leu Ser Ser Gly Met Val Leu Val Phe
305                 310                 315                 320

Ser Ile Trp Asn Asp Asn Ser Gln Tyr Met Asn Trp Leu Asp Ser Gly
                    325                 330                 335

Asn Ala Gly Pro Cys Ser Ser Thr Glu Gly Asn Pro Ser Asn Ile Leu
                    340                 345                 350

Ala Asn Asn Pro Asn Thr His Val Val Phe Ser Asn Ile Arg Trp Gly
                    355                 360                 365

Asp Ile Gly Ser Thr Thr Asn Ser Thr Ala Pro Pro Pro Pro Ala
370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
                    405                 410                 415

Tyr Ser Gly Cys Lys Thr Cys Thr Ser Gly Thr Thr Cys Gln Tyr Ser
                    420                 425                 430

Asn Asp Tyr Tyr Ser Gln Cys Leu
                    435                 440

<210> SEQ ID NO 21
<211> LENGTH: 1320
<212> TYPE: DNA
<213> ORGANISM: Artificial Sequence
```

<220> FEATURE:
<223> OTHER INFORMATION: 11G8

<400> SEQUENCE: 21

```
cagcaaccgg gtaccagcac ccccgaggtc catcccaagt tgacaaccta caagtgtaca    60
aagtccgggg ggtgcgtggc ccaggacacc tcggtggtcc ttgactggaa ctaccgctgg   120
atgcacgacg caaactacaa ctcgtgcacc gtcaacggcg gcgtcaacac cacgctctgc   180
cctgacgagg cgacctgtgg caagaactgc ttcatcgagg cgtcgactac cgccgcctcg   240
ggcgtcacga cctcgggcag cagcctcacc ctgaggcagt tcgtcaagga cagcgagggc   300
aagaccaaca cgctctctcc tcgggcctat ctcctgggcg ccgacggtga ctacgtgatg   360
ttcaagctcc tcaaccagga gctgagcttc gacgtcgacg tctctacgct gccgtgtgga   420
gagaacgcag cgctctactt ctctgagatg gacaagaccg ggggccgcaa cgaatataac   480
acgggcggtg ccgagtacgg gagcggctac tgcgatgctc agtgccccgt ccagacatgg   540
aacaacggca ccctcaacac tagccaccag ggctcgtgct gcaacgagat ggatatcctg   600
gaggccaact cgaaggcgga agccttcacc cctcacccct gcatcggcga caactgcgac   660
aagggcggtt gcggcttcaa ctcgtatgcg cgcggcaaca aaaactactg gcgcccggga   720
ggcaccctcg acacctccaa gccctttcacc atggtgaccc agttcatcac ggacgacggc   780
accagctcgg gcaagcttag ccagatcgtg cgctcctacg tgcaaaacgg ccagaaggtc   840
gccagcgccg tgtccggcgg cgacagcatc accgtcgagg gctgctcgtc ctccgacgcc   900
tacgcgggcc tcgtcggtat gggcgaggcc ctgggccgcg gcatggtgct cgtgttcagc   960
atttggaacg acaacagcca gtacatgaac tggctcgaca gcggcaacgc cggcccctgc  1020
agcagcaccg agggcaaccc atccaacatc tggccaaca accccaacac gcacgtcgtc  1080
ttctccaaca tccgctgggg agacattggg tctactacga actcgactgc gccccgccc  1140
ccgcctgcgt ccagcacgac gttttcgact acacggagga gctcgacgac ttcgagcagc  1200
ccgagctgca cgcagactca ctgggggcag tgcggtggca ttgggtacag cgggtgcaag  1260
acgtgcacgt cgggcactac gtgccagtat agcaacgact actactcgca atgcctttaa  1320
```

<210> SEQ ID NO 22
<211> LENGTH: 439
<212> TYPE: PRT
<213> ORGANISM: Artificial Sequence
<220> FEATURE:
<223> OTHER INFORMATION: 11G8

<400> SEQUENCE: 22

```
Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
            20                  25                  30

Val Leu Asp Trp Asn Tyr Arg Trp Met His Asp Ala Asn Tyr Asn Ser
        35                  40                  45

Cys Thr Val Asn Gly Val Asn Thr Thr Leu Cys Pro Asp Glu Ala
    50                  55                  60

Thr Cys Gly Lys Asn Cys Phe Ile Glu Gly Val Asp Tyr Ala Ala Ser
65                  70                  75                  80

Gly Val Thr Thr Ser Gly Ser Ser Leu Thr Leu Arg Gln Phe Val Lys
                85                  90                  95

Asp Ser Glu Gly Lys Thr Asn Ser Val Ser Pro Arg Ala Tyr Leu Leu
            100                 105                 110
```

-continued

Gly Ala Asp Gly Asp Tyr Val Met Phe Lys Leu Leu Asn Gln Glu Leu
        115                 120                 125

Ser Phe Asp Val Asp Val Ser Thr Leu Pro Cys Gly Glu Asn Ala Ala
130                 135                 140

Leu Tyr Phe Ser Glu Met Asp Lys Thr Gly Gly Arg Asn Glu Tyr Asn
145                 150                 155                 160

Thr Gly Gly Ala Glu Tyr Gly Ser Gly Tyr Cys Asp Ala Gln Cys Pro
                165                 170                 175

Val Gln Thr Trp Asn Asn Gly Thr Leu Asn Thr Ser His Gln Gly Ser
            180                 185                 190

Cys Cys Asn Glu Met Asp Ile Leu Glu Ala Asn Ser Lys Ala Glu Ala
        195                 200                 205

Phe Thr Pro His Pro Cys Ile Gly Asp Asn Cys Asp Lys Gly Gly Cys
    210                 215                 220

Gly Phe Asn Ser Tyr Ala Arg Gly Asn Lys Asn Tyr Trp Ala Pro Gly
225                 230                 235                 240

Gly Thr Leu Asp Thr Ser Lys Pro Phe Thr Met Val Thr Gln Phe Ile
                245                 250                 255

Thr Asp Asp Gly Thr Ser Ser Gly Lys Leu Ser Gln Ile Val Arg Ser
            260                 265                 270

Tyr Val Gln Asn Gly Gln Lys Val Ala Ser Ala Val Ser Gly Gly Asp
        275                 280                 285

Ser Ile Thr Val Glu Gly Cys Ser Ser Ser Ala Tyr Gly Gly Leu
    290                 295                 300

Val Gly Met Gly Glu Ala Leu Gly Arg Gly Met Val Leu Val Phe Ser
305                 310                 315                 320

Ile Trp Asn Asp Asn Ser Gln Tyr Met Asn Trp Leu Asp Ser Gly Asn
                325                 330                 335

Ala Gly Pro Cys Ser Ser Thr Glu Gly Asn Pro Ser Asn Ile Leu Ala
            340                 345                 350

Asn Asn Pro Asn Thr His Val Val Phe Ser Asn Ile Arg Trp Gly Asp
        355                 360                 365

Ile Gly Ser Thr Thr Asn Ser Thr Ala Pro Pro Pro Pro Ala Ser
    370                 375                 380

Ser Thr Thr Phe Ser Thr Thr Arg Arg Ser Ser Thr Thr Ser Ser Ser
385                 390                 395                 400

Pro Ser Cys Thr Gln Thr His Trp Gly Gln Cys Gly Gly Ile Gly Tyr
                405                 410                 415

Ser Gly Cys Lys Thr Cys Thr Ser Gly Thr Thr Cys Gln Tyr Ser Asn
            420                 425                 430

Asp Tyr Tyr Ser Gln Cys Leu
        435

<210> SEQ ID NO 23
<211> LENGTH: 1317
<212> TYPE: DNA
<213> ORGANISM: Artificial Sequence
<220> FEATURE:
<223> OTHER INFORMATION: 92A12

<400> SEQUENCE: 23
cagcaaccgg gtaccagcac ccccgaggtc catcccaagt tgacaaccta caagtgtaca      60
aagtccgggg ggtgcgtggc ccaggacacc tcggtggtcc ttgactggaa ctaccgctgg     120
atgcacgacg caaactacaa ctcgtgcacc gtcaacggcg gcgtcaacac cacgctctgc     180

-continued

```
cctgacgcgg cgacctgtgc gaagaactgc gtgatcgagc cggccaacta caccagcgcc      240
ggcgtcacga cctcgggcga cagcctcacc atgtaccagt acgttcagag caacggcgtc      300
tacaccaacg cctctcctcg ggcctatctc ctgggcgccg acggtgacta cgtgatgttc      360
aagctcctca accaggagct gagcttcgac gtcgacgtct ctacgctgcc gtgtggagag      420
aacgcagcgc tctacttctc tgagatggac aagaccgggg ccggaacga gcacaacacg       480 ggcggtgcca gtacgggag cggctactgc gatgctcagt gccccgtcca gacatggaac       540
aacggcaccc tcaacactag ccaccagggc tcgtgctgca acgagatgga tatcctggag      600
gccaactcga aggcggaagc cttcaccccct caccccctgca tcggcgacaa ctgcgacaag    660
ggcggttgcg gcttcaactc gtatgcgcgc ggcaacaaaa actactgggc gcccggaggc      720
accctcgaca cctccaagcc cttcaccatg gtgacccagt tcatcacgga cgacggcacc      780
agctcgggca agcttagcca gatcgtgcgc tcctacgtgc aaaacggcca gaaggtcgcc      840
agcgccgtgt ccggcggcga cagcatcacc gtcgagggct gctcgtcctc cgacgcctac     900
ggcggcctcg tcggtatggg cgaggccctg gccgcggca tggtgctcgt gttcagcatt      960
tggaacgaca cagccagta catgaactgg ctcgacagcg gcaacgccgg ccctgcagc       1020 agcaccgagg gcaacccatc caacatcctg gccaacaacc caacacgca cgtcgtcttc      1080 tccaacatcc gctggggaga cattgggtct actacgaact cgactgcgcc cccgccccg      1140 cctgcgtcca gcacgacgtt ttcgactaca cggaggagct cgacgacttc gagcagcccg    1200
agctgcacgc agactcactg ggggcagtgc ggtggcattg ggtacagcgg gtgcaagacg    1260
tgcacgtcgg gcactacgtg ccagtatagc aacgactact actcgcaatg cctttaa      1317
```

<210> SEQ ID NO 24
<211> LENGTH: 438
<212> TYPE: PRT
<213> ORGANISM: Artificial Sequence
<220> FEATURE:
<223> OTHER INFORMATION: 92A12

<400> SEQUENCE: 24

```
Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
            20                  25                  30

Val Leu Asp Trp Asn Tyr Arg Trp Met His Asp Ala Asn Tyr Asn Ser
        35                  40                  45

Cys Thr Val Asn Gly Gly Val Asn Thr Thr Leu Cys Pro Asp Ala Ala
    50                  55                  60

Thr Cys Ala Lys Asn Cys Val Ile Glu Pro Ala Asn Tyr Thr Ser Ala
65                  70                  75                  80

Gly Val Thr Thr Ser Gly Asp Ser Leu Thr Met Tyr Gln Tyr Val Gln
                85                  90                  95

Ser Asn Gly Val Tyr Thr Asn Ala Ser Pro Arg Ala Tyr Leu Leu Gly
            100                 105                 110

Ala Asp Gly Asp Tyr Val Met Phe Lys Leu Leu Asn Gln Glu Leu Ser
        115                 120                 125

Phe Asp Val Asp Val Ser Thr Leu Pro Cys Gly Glu Asn Ala Ala Leu
    130                 135                 140

Tyr Phe Ser Glu Met Asp Lys Thr Gly Gly Arg Asn Glu His Asn Thr
145                 150                 155                 160
```

Gly Gly Ala Lys Tyr Gly Ser Gly Tyr Cys Asp Ala Gln Cys Pro Val
            165                 170                 175

Gln Thr Trp Asn Asn Gly Thr Leu Asn Thr Ser His Gly Ser Cys
        180                 185                 190

Cys Asn Glu Met Asp Ile Leu Glu Ala Asn Ser Lys Ala Glu Ala Phe
            195                 200                 205

Thr Pro His Pro Cys Ile Gly Asp Asn Cys Asp Lys Gly Cys Gly
        210                 215                 220

Phe Asn Ser Tyr Ala Arg Gly Asn Lys Asn Tyr Trp Ala Pro Gly Gly
225                 230                 235                 240

Thr Leu Asp Thr Ser Lys Pro Phe Thr Met Val Thr Gln Phe Ile Thr
                245                 250                 255

Asp Asp Gly Thr Ser Ser Gly Lys Leu Ser Gln Ile Val Arg Ser Tyr
            260                 265                 270

Val Gln Asn Gly Gln Lys Val Ala Ser Ala Val Ser Gly Gly Asp Ser
        275                 280                 285

Ile Thr Val Glu Gly Cys Ser Ser Asp Ala Tyr Gly Gly Leu Val
        290                 295                 300

Gly Met Gly Glu Ala Leu Gly Arg Gly Met Val Leu Val Phe Ser Ile
305                 310                 315                 320

Trp Asn Asp Asn Ser Gln Tyr Met Asn Trp Leu Asp Ser Gly Asn Ala
                325                 330                 335

Gly Pro Cys Ser Ser Thr Glu Gly Asn Pro Ser Asn Ile Leu Ala Asn
            340                 345                 350

Asn Pro Asn Thr His Val Val Phe Ser Asn Ile Arg Trp Gly Asp Ile
        355                 360                 365

Gly Ser Thr Thr Asn Ser Thr Ala Pro Pro Pro Pro Ala Ser Ser
370                 375                 380

Thr Thr Phe Ser Thr Thr Arg Arg Ser Ser Thr Thr Ser Ser Ser Pro
385                 390                 395                 400

Ser Cys Thr Gln Thr His Trp Gly Gln Cys Gly Gly Ile Gly Tyr Ser
                405                 410                 415

Gly Cys Lys Thr Cys Thr Ser Gly Thr Thr Cys Gln Tyr Ser Asn Asp
            420                 425                 430

Tyr Tyr Ser Gln Cys Leu
            435

<210> SEQ ID NO 25
<211> LENGTH: 1320
<212> TYPE: DNA
<213> ORGANISM: Artificial Sequence
<220> FEATURE:
<223> OTHER INFORMATION: 240H12

<400> SEQUENCE: 25

```
cagcaaccgg gtaccagcac ccccgaggtc catcccaagt tgacaaccta caagtgtaca      60
actgctgggg ggtgcgtggc ccaggacacc tcggtggtcc ttgactgggg ctaccactgg     120
attcacacgg tcgatgggta cacatcgtgc accacatcgt ccggcgtcga cagcacgctc     180
tgccctgacg cggcgacctg tgcgaagaac tgcgtgatcg agccggccaa ctacaccagc     240
gccggcgtca cgacctcggg cgacagcctc accatgtacc agtacgttca gagcaacggc     300
gtctacacca cgcctctcc tcgggcctat ctcctgggcg ccgacggtga ctacgtgatg     360
ttcaagctcc tcaaccagga gctgagcttc gacgtcgacg tctctacgct gccgtgtgga     420
gagaacgcag cgctctactt ctctgagatg gacaagaccg ggggccggaa cgagcacaac     480
```

```
acgggcggtg ccaagtacgg gagcggctac tgcgatgctc agtgccccgt ccagacatgg    540
aacaacggca ccctcaacac tagccaccag ggctcgtgct gcaacgagat ggatatcctg    600
gaggccaact cgaaggcgga agccttcacc cctcaccct gcatcggcga caactgcgac     660
aagggcggtt gcggcttcaa ctcgtatgcg cgcggcaaca aaaactactg ggcgcccgga    720
ggcaccctcg acacctccaa gcccttcacc atggtgaccc agttcatcac ggacgacggc    780
accagctcgg gcaagcttag ccagatcgtg cgctcctacg tgcaaaacgg ccagaaggtc    840
gccagcgccg tgtccggcgg cgacagcatc accgtcgagg gctgctcgtc cgcctcagcc    900
tacgccggcc tcgccaccat gggcaaggcc ctgagcagcg catggtgct cgtgttcagc     960 atttggaacg acaacagcca gtacatgaac tggctcgaca gcggcaacgc cggcccctgc   1020
agcagcaccg agggcaaccc atccaacatc ctggccaaca accccaacac gcacgtcgtc   1080
ttctccaaca tccgctgggg agacattggg tctactacga actcgactgc gcccccgccc   1140
ccgcctgcgt ccagcacgac gttttcgact acacggagga gctcgacgac ttcgagcagc   1200
ccgagctgca cgcagactca ctgggggcag tgcggtggca ttgggtacag cgggtgcaag   1260
acgtgcacgt cgggcactac gtgccagtat agcaacgact actactcgca atgcctttaa   1320
```

```
<210> SEQ ID NO 26
<211> LENGTH: 439
<212> TYPE: PRT
<213> ORGANISM: Artificial Sequence
<220> FEATURE:
<223> OTHER INFORMATION: 240H12

<400> SEQUENCE: 26
```

| Gln | Gln | Pro | Gly | Thr | Ser | Thr | Pro | Glu | Val | His | Pro | Lys | Leu | Thr | Thr |
|---|---|---|---|---|---|---|---|---|---|---|---|---|---|---|---|
| 1 | | | | 5 | | | | | 10 | | | | | 15 | |

| Tyr | Lys | Cys | Thr | Thr | Ala | Gly | Gly | Cys | Val | Ala | Gln | Asp | Thr | Ser | Val |
|---|---|---|---|---|---|---|---|---|---|---|---|---|---|---|---|
| | | | 20 | | | | | 25 | | | | 30 | | | |

| Val | Leu | Asp | Trp | Gly | Tyr | His | Trp | Ile | His | Thr | Val | Asp | Gly | Tyr | Thr |
|---|---|---|---|---|---|---|---|---|---|---|---|---|---|---|---|
| | | | 35 | | | | 40 | | | | | 45 | | | |

| Ser | Cys | Thr | Thr | Ser | Ser | Gly | Val | Asp | Ser | Thr | Leu | Cys | Pro | Asp | Ala |
|---|---|---|---|---|---|---|---|---|---|---|---|---|---|---|---|
| | 50 | | | | | 55 | | | | | 60 | | | | |

| Ala | Thr | Cys | Ala | Lys | Asn | Cys | Val | Ile | Glu | Pro | Ala | Asn | Tyr | Thr | Ser |
|---|---|---|---|---|---|---|---|---|---|---|---|---|---|---|---|
| 65 | | | | | 70 | | | | | 75 | | | | | 80 |

| Ala | Gly | Val | Thr | Thr | Ser | Gly | Asp | Ser | Leu | Thr | Met | Tyr | Gln | Tyr | Val |
|---|---|---|---|---|---|---|---|---|---|---|---|---|---|---|---|
| | | | | 85 | | | | | 90 | | | | | 95 | |

| Gln | Ser | Asn | Gly | Val | Tyr | Thr | Asn | Ala | Ser | Pro | Arg | Ala | Tyr | Leu | Leu |
|---|---|---|---|---|---|---|---|---|---|---|---|---|---|---|---|
| | | | 100 | | | | | 105 | | | | 110 | | | |

| Gly | Ala | Asp | Gly | Asp | Tyr | Val | Met | Phe | Lys | Leu | Leu | Asn | Gln | Glu | Leu |
|---|---|---|---|---|---|---|---|---|---|---|---|---|---|---|---|
| | | | 115 | | | | 120 | | | | | 125 | | | |

| Ser | Phe | Asp | Val | Asp | Val | Ser | Thr | Leu | Pro | Cys | Gly | Glu | Asn | Ala | Ala |
|---|---|---|---|---|---|---|---|---|---|---|---|---|---|---|---|
| | 130 | | | | | 135 | | | | | 140 | | | | |

| Leu | Tyr | Phe | Ser | Glu | Met | Asp | Lys | Thr | Gly | Gly | Arg | Asn | Glu | His | Asn |
|---|---|---|---|---|---|---|---|---|---|---|---|---|---|---|---|
| 145 | | | | | 150 | | | | | 155 | | | | | 160 |

| Thr | Gly | Gly | Ala | Lys | Tyr | Gly | Ser | Gly | Tyr | Cys | Asp | Ala | Gln | Cys | Pro |
|---|---|---|---|---|---|---|---|---|---|---|---|---|---|---|---|
| | | | | 165 | | | | | 170 | | | | | 175 | |

| Val | Gln | Thr | Trp | Asn | Asn | Gly | Thr | Leu | Asn | Thr | Ser | His | Gln | Gly | Ser |
|---|---|---|---|---|---|---|---|---|---|---|---|---|---|---|---|
| | | | 180 | | | | | 185 | | | | 190 | | | |

| Cys | Cys | Asn | Glu | Met | Asp | Ile | Leu | Glu | Ala | Asn | Ser | Lys | Ala | Glu | Ala |
|---|---|---|---|---|---|---|---|---|---|---|---|---|---|---|---|
| | | 195 | | | | | 200 | | | | | 205 | | | |

| Phe | Thr | Pro | His | Pro | Cys | Ile | Gly | Asp | Asn | Cys | Asp | Lys | Gly | Gly | Cys |

```
                    210                 215                 220
Gly Phe Asn Ser Tyr Ala Arg Gly Asn Lys Asn Tyr Trp Ala Pro Gly
225                 230                 235                 240

Gly Thr Leu Asp Thr Ser Lys Pro Phe Thr Met Val Thr Gln Phe Ile
            245                 250                 255

Thr Asp Asp Gly Thr Ser Ser Gly Lys Leu Ser Gln Ile Val Arg Ser
                260                 265                 270

Tyr Val Gln Asn Gly Gln Lys Val Ala Ser Ala Val Ser Gly Gly Asp
            275                 280                 285

Ser Ile Thr Val Glu Gly Cys Ser Ser Ala Ser Ala Tyr Gly Gly Leu
        290                 295                 300

Ala Thr Met Gly Lys Ala Leu Ser Ser Gly Met Val Leu Val Phe Ser
305                 310                 315                 320

Ile Trp Asn Asp Asn Ser Gln Tyr Met Asn Trp Leu Asp Ser Gly Asn
                325                 330                 335

Ala Gly Pro Cys Ser Ser Thr Glu Gly Asn Pro Ser Asn Ile Leu Ala
            340                 345                 350

Asn Asn Pro Asn Thr His Val Val Phe Ser Asn Ile Arg Trp Gly Asp
        355                 360                 365

Ile Gly Ser Thr Thr Asn Ser Thr Ala Pro Pro Pro Pro Ala Ser
    370                 375                 380

Ser Thr Thr Phe Ser Thr Thr Arg Arg Ser Ser Thr Thr Ser Ser Ser
385                 390                 395                 400

Pro Ser Cys Thr Gln Thr His Trp Gly Gln Cys Gly Gly Ile Gly Tyr
                405                 410                 415

Ser Gly Cys Lys Thr Cys Thr Ser Gly Thr Thr Cys Gln Tyr Ser Asn
            420                 425                 430

Asp Tyr Tyr Ser Gln Cys Leu
            435

<210> SEQ ID NO 27
<211> LENGTH: 1131
<212> TYPE: DNA
<213> ORGANISM: Chaetomium globosum

<400> SEQUENCE: 27
cagcaaccgg gttcggtgac ccccgaggtc catcccaagt tgcccacctg cagtgtaca      60 aagtccgggg ggtgcgtgga gcaggacacc tcggtggtcc ttgactggaa ctaccgctgg    120
ttccacacct cggacaacac cacctcgtgc accacgtcct cgggcatcga ctcgacgctc    180
tgccctgacg cagcgacctg tgccgagaac tgcgtcgtgg agggcaccga ctacaccagc    240
tcgggcatcg agacctcggg cagcagcctc accctgaggc agttcgtcaa ggacagcgag    300
ggcaagacca acagcgtctc tcctcgggcc tatctcctgg cgccgacggt gactacgtg     360 atgttcaagc tcctcaacca ggagctgagc ttcgacgtcg acgtctctac gctgccgtgt    420
ggagagaaca cagcgctcta cttctctgag atggacaaga ccgggggccg gaacgagcac    480
aacacgggcg gtgccaagta cgggagcggc tactgcgatg ctcagtgccc cgtccagaca    540
tggaacaacg gcaccctcaa cactagccac cagggctcgt gctgcaacga gatggatatc    600
ctggaggcca actcgaaggc ggaagccttc accctcacc cctgcatcgg cgacaactgc    660
gacaagggcg gttgcggctt caactcgtat gcggcgcggca acaaaaacta ctgggcgccc    720
ggaggcaccc tcgacacctc caagcccttc accatggtga cccagttcat cacgacgac    780 ggcaccagct cgggcaagct tagccagatc gtgcgctcct acgtgcaaaa cggccagaag    840
```

```
gtcgccagcg ccgtgtccgg cggcgacagc atcaccgtcg agggctgctc gtcctccgac    900
gcctacggcg gcctcgtcgg tatgggcgag gccctgggcc gcggcatggt gctcgccatg    960
agcatttgga cgacgccag cggcttcatg aactggctcg acagcggcga caacggcccc   1020
tgcaacgaga ccgagggcga cccagccaac atcctggcca ccaccccga ttcgcaggtc   1080
gtcctgtcca acatccgctg gggagacatt gactctactg ttcagctcta a           1131
```

<210> SEQ ID NO 28
<211> LENGTH: 376
<212> TYPE: PRT
<213> ORGANISM: Chaetomium globosum

<400> SEQUENCE: 28

```
Gln Gln Pro Gly Ser Val Thr Pro Glu Val His Pro Lys Leu Pro Thr
1               5                   10                  15

Trp Gln Cys Thr Lys Ser Gly Gly Cys Val Glu Gln Asp Thr Ser Val
            20                  25                  30

Val Leu Asp Trp Asn Tyr Arg Trp Phe His Thr Ser Asp Asn Thr Thr
        35                  40                  45

Ser Cys Thr Thr Ser Ser Gly Ile Asp Ser Thr Leu Cys Pro Asp Ala
    50                  55                  60

Ala Thr Cys Ala Glu Asn Cys Val Val Glu Gly Thr Asp Tyr Thr Ser
65                  70                  75                  80

Ser Gly Ile Glu Thr Ser Gly Ser Ser Leu Thr Leu Arg Gln Phe Val
                85                  90                  95

Lys Asp Ser Glu Gly Lys Thr Asn Ser Val Ser Pro Arg Ala Tyr Leu
            100                 105                 110

Leu Gly Ala Asp Gly Asp Tyr Val Met Phe Lys Leu Leu Asn Gln Glu
        115                 120                 125

Leu Ser Phe Asp Val Asp Val Ser Thr Leu Pro Cys Gly Glu Asn Ala
    130                 135                 140

Ala Leu Tyr Phe Ser Glu Met Asp Lys Thr Gly Gly Arg Asn Glu His
145                 150                 155                 160

Asn Thr Gly Gly Ala Lys Tyr Gly Ser Gly Tyr Cys Asp Ala Gln Cys
                165                 170                 175

Pro Val Gln Thr Trp Asn Asn Gly Thr Leu Asn Thr Ser His Gln Gly
            180                 185                 190

Ser Cys Cys Asn Glu Met Asp Ile Leu Glu Ala Asn Ser Lys Ala Glu
        195                 200                 205

Ala Phe Thr Pro His Pro Cys Ile Gly Asp Asn Cys Asp Lys Gly Gly
    210                 215                 220

Cys Gly Phe Asn Ser Tyr Ala Arg Gly Asn Lys Asn Tyr Trp Ala Pro
225                 230                 235                 240

Gly Gly Thr Leu Asp Thr Ser Lys Pro Phe Thr Met Val Thr Gln Phe
                245                 250                 255

Ile Thr Asp Asp Gly Thr Ser Ser Gly Lys Leu Ser Gln Ile Val Arg
            260                 265                 270

Ser Tyr Val Gln Asn Gly Gln Lys Val Ala Ser Ala Val Ser Gly Gly
        275                 280                 285

Asp Ser Ile Thr Val Glu Gly Cys Ser Ser Ser Asp Ala Tyr Gly Gly
    290                 295                 300

Leu Val Gly Met Gly Glu Ala Leu Gly Arg Gly Met Val Leu Ala Met
305                 310                 315                 320
```

Ser Ile Trp Asn Asp Ala Ser Gly Phe Met Asn Trp Leu Asp Ser Gly
            325                 330                 335

Asp Asn Gly Pro Cys Asn Glu Thr Glu Gly Asp Pro Ala Asn Ile Leu
        340                 345                 350

Ala Asn His Pro Asp Ser Gln Val Val Leu Ser Asn Ile Arg Trp Gly
        355                 360                 365

Asp Ile Asp Ser Thr Val Gln Leu
        370                 375

<210> SEQ ID NO 29
<211> LENGTH: 1323
<212> TYPE: DNA
<213> ORGANISM: Aspergillus fumigatus

<400> SEQUENCE: 29

| | |
|---|---:|
| cagcaaccgg ccgcgagttc tgctggtaac cccaagttga caacctacaa gtgtacaact | 60 |
| gctgggggt gcgtggccca ggacacctcg gtggtccttg actggggcta ccactggatt | 120 |
| cacacggtcg atgggtacac atcgtgcacc acatcgtccg cgtcgacag cacgctctgc | 180 |
| cctgacgcgg cgacctgtgc gaagaactgc gtgatcgagc cggccaacta ccagcgcc | 240 |
| ggcgtcacga cctcgggcga cagcctcacc atgtaccagt acgttcagag caacggcgtc | 300 |
| tacaccaacg cctctcctcg gctgtatctc ctgggcccg acaagaacta cgtgatgctg | 360 |
| aagctcctag gccaggagct gaccttcgac gtcgacctct ctacactgcc gtgtggagag | 420 |
| aacggcgccc tctacctgtc tgaaatgagc gccaccgggg ccgcaacga atataacacg | 480 |
| ggcggtgcca agtacgggag cggctactgc gatgctcagt gccccgtcat cgcctggaag | 540 |
| aacggcaccc tcaacactag cggcgcaagc tactgctgca cgagatgga tatcctggag | 600 |
| gccaactcga gggcgaattc gtacacccct cacccctgca gtgccacgga ctgcgacaag | 660 |
| ggcggttgcg gcttcaaccc ctatgctctc ggccaaaaaa gctactgggg ccccggaggc | 720 |
| accgttgaca cctccaagcc cttcaccatc accacccagt tcatcacgaa cgacggcacc | 780 |
| accaccggca ccctttccga aatccgccgc cagtacatgc aaaacggcaa ggtgatcgcc | 840 |
| aatgccgttt cctccactgg cgtcaactcc atcaccgagg actggtgcac gtccgtcgac | 900 |
| ggctcggccg ccacctttgg cggcctcacc accatgggca aggccctggg ccgcggcatg | 960 |
| gtgctcatct tcagcatttg gaacgacgcc agcggcttta tgaactggct cgacagcggc | 1020 |
| aacgccggcc cctgcagcag caccgagggc aacccagact tgatcaaggc ccagaacccc | 1080 |
| acgacgcacg tcgtcttctc caacatccgc tggggagaca ttgggtctac tttcaagggt | 1140 |
| tctgatggct cggtgacgac gacgacgtcg actacatcga ccaagaccac gacttcgacc | 1200 |
| gcgccggggc caacgcagac tcactatggg cagtgcggtg gccaagggtg gactgggccc | 1260 |
| acggcttgcg catcgcccta cacgtgccag gttctgaacc cgtggtactc gcaatgcctt | 1320 |
| taa | 1323 |

<210> SEQ ID NO 30
<211> LENGTH: 440
<212> TYPE: PRT
<213> ORGANISM: Aspergillus fumigatus

<400> SEQUENCE: 30

Gln Gln Pro Ala Ala Ser Ser Ala Gly Asn Pro Lys Leu Thr Thr Tyr
1               5                   10                  15

Lys Cys Thr Thr Ala Gly Gly Cys Val Ala Gln Asp Thr Ser Val Val
            20                  25                  30

-continued

```
Leu Asp Trp Gly Tyr His Trp Ile His Thr Val Asp Gly Tyr Thr Ser
         35                  40                  45
Cys Thr Thr Ser Ser Gly Val Asp Ser Thr Leu Cys Pro Asp Ala Ala
 50                  55                  60
Thr Cys Ala Lys Asn Cys Val Ile Glu Pro Ala Asn Tyr Thr Ser Ala
 65                  70                  75                  80
Gly Val Thr Thr Ser Gly Asp Ser Leu Thr Met Tyr Gln Tyr Val Gln
                 85                  90                  95
Ser Asn Gly Val Tyr Thr Asn Ala Ser Pro Arg Leu Tyr Leu Leu Gly
                100                 105                 110
Pro Asp Lys Asn Tyr Val Met Leu Lys Leu Leu Gly Gln Glu Leu Thr
            115                 120                 125
Phe Asp Val Asp Leu Ser Thr Leu Pro Cys Gly Glu Asn Gly Ala Leu
    130                 135                 140
Tyr Leu Ser Glu Met Ser Ala Thr Gly Gly Arg Asn Glu Tyr Asn Thr
145                 150                 155                 160
Gly Gly Ala Glu Tyr Gly Ser Gly Tyr Cys Asp Ala Gln Cys Pro Val
                165                 170                 175
Ile Ala Trp Lys Asn Gly Thr Leu Asn Thr Ser Gly Ala Ser Tyr Cys
            180                 185                 190
Cys Asn Glu Met Asp Ile Leu Glu Ala Asn Ser Arg Ala Asn Ser Tyr
    195                 200                 205
Thr Pro His Pro Cys Ser Ala Thr Asp Cys Asp Lys Gly Gly Cys Gly
210                 215                 220
Phe Asn Pro Tyr Ala Leu Gly Gln Lys Ser Tyr Trp Gly Pro Gly Gly
225                 230                 235                 240
Thr Val Asp Thr Ser Lys Pro Phe Thr Ile Thr Thr Gln Phe Ile Thr
                245                 250                 255
Asn Asp Gly Thr Thr Thr Gly Thr Leu Ser Glu Ile Arg Arg Gln Tyr
            260                 265                 270
Met Gln Asn Gly Lys Val Ile Ala Asn Ala Val Ser Ser Thr Gly Val
    275                 280                 285
Asn Ser Ile Thr Glu Asp Trp Cys Thr Ser Val Asp Gly Ser Ala Ala
290                 295                 300
Thr Phe Gly Gly Leu Thr Thr Met Gly Lys Ala Leu Gly Arg Gly Met
305                 310                 315                 320
Val Leu Ile Phe Ser Ile Trp Asn Asp Ala Ser Gly Phe Met Asn Trp
                325                 330                 335
Leu Asp Ser Gly Asn Ala Gly Pro Cys Ser Ser Thr Glu Gly Asn Pro
            340                 345                 350
Asp Leu Ile Lys Ala Gln Asn Pro Thr Thr His Val Val Phe Ser Asn
    355                 360                 365
Ile Arg Trp Gly Asp Ile Gly Ser Thr Phe Lys Gly Ser Asp Gly Ser
370                 375                 380
Val Thr Thr Thr Thr Ser Thr Thr Ser Thr Lys Thr Thr Thr Ser Thr
385                 390                 395                 400
Ala Pro Gly Pro Thr Gln Thr His Tyr Gly Gln Cys Gly Gly Gln Gly
                405                 410                 415
Trp Thr Gly Pro Thr Ala Cys Ala Ser Pro Tyr Thr Cys Gln Val Leu
            420                 425                 430
Asn Pro Trp Tyr Ser Gln Cys Leu
    435                 440
```

ENDOGLUCANASE VARIANTS HAVING IMPROVED ACTIVITY, AND USES OF SAME

This application is a U.S. national phase of International Application No. PCT/FR2014/052984, filed Nov. 21, 2014, which claims priority from French Patent application no. FR1361509, filed Nov. 22, 2013, the disclosure of each of which is hereby incorporated by reference in its entirety.

The possibility of producing ethanol from cellulose has received a great deal of attention owing to the availability of large amounts of raw material and also the value of ethanol as a fuel. The cellulose-based natural raw materials for such a process are denoted "biomass". Many types of biomass, for example wood, agricultural residues, herbaceous crops and municipal solid waste, have been considered as potential raw materials for producing biofuel. These materials consist mainly of cellulose, hemicellulose and lignin.

Cellulose is a polymer consisting of glucose molecules linked by beta-1,4 bonds, which are very resistant to breakdown or to depolymerization. Once the cellulose has been converted to glucose, the latter is easily fermented to biofuel, for example ethanol, using a yeast.

The oldest methods studied for converting the cellulose to glucose are based on acid hydrolysis. This process can be carried out in the presence of concentrated or dilute acids. However, several drawbacks, such as poor recovery of the acid when concentrated acids are used and the low production of glucose in the case of the use of dilute acids, are detrimental to the economy of the acid hydrolysis process.

To overcome the drawbacks of the acid hydrolysis process, cellulose conversion processes have more recently related to enzymatic hydrolysis, using enzymes of cellulase type. This enzymatic hydrolysis of lignocellulosic biomass (for example, cellulose) has, however, the drawback of being an expensive industrial process. As a result, it is necessary to use increasingly effective cellulase-secreting microorganism strains. In this respect, many microorganisms comprise enzymes which hydrolyze cellulose, such as the fungi *Trichoderma*, *Aspergillus*, *Humicola* or *Fusarium* and also bacteria such as *Thermomonospora*, *Bacillus*, *Cellulomonas* and *Streptomyces*. The enzymes secreted by these microorganisms have three types of activities that are useful in the conversion of cellulose to glucose and are divided up into three groups: endoglucanases, which randomly attack cellulose fibers internally, exoglucanases which will attack the ends of the fibers, releasing cellobiose, and β-glucosidases which will hydrolyze this cellobiose to glucose. Other classes of enzymes such as hemicellulases or the recently discovered polysaccharide monooxygenase enzyme class can also play a role in the efficiency of the hydrolysis.

There is a strong industrial interest in decreasing the cost of enzymatic hydrolysis, and this decrease involves the use of a reduced amount of enzymes and therefore cocktails of enzymes that are more effective. Consequently, several patent applications describe natural enzymes with capacities greater than those of *Trichoderma reesei* or variants that have been improved by genetic engineering. Mention may be made of patent applications US2010304464, WO 2010/066411 and WO 2013/029176 relating to exoglucanases, applications WO 2007/109441, WO 2012/149192 and WO 2010/076388 relating to endoglucanases, applications WO 2010/029259, WO 2010/135836 or WO 2010/022518 relating to beta-glucosidases, or else applications WO12135659 and WO12149344 relating to polysaccharide monooxygenases.

Enzymes which hydrolyze lignocellulosic biomass are classified in the CAZy system (Cantarel, B. L., Coutinho, P. M., Rancurel, C., Bernard, T., Lombard, V., & Henrissat, B. (2009). The Carbohydrate-Active EnZymes database (CAZy): an expert resource for Glycogenomics. Nucleic acids research, 37, D233-8) on the basis of principally structural criteria. Endoglucanases can belong to the families GH 5, 6, 7, 8, 9, 12, 16, 18, 19, 26, 44, 45, 48, 51, 74 and 124.

In order for a hydrolysis of the lignocellulosic biomass to be effective and economically comfortable, the enzymatic mixture must comprise equilibrated proportions of enzymes having diverse enzymatic activities, inter alia, but not exclusively, of the exoglucanase, endoglucanase, xylanase and β-glucosidase type. By way of example, in the native mixtures of *Trichoderma reesei*, the presence of 60-70% of exoglucanases, 15-20% of endoglucanases, a few percentages of hemicellulases and approximately 5-10% of β-glucosidases are generally noted. This mixture is suitable for hydrolyzing the majority of pretreated substrates (for example such as wheat straw steam-exploded under acid conditions) with acceptable yields. In short, the increase in the endoglucanase activity must not take place to the detriment of the other enzymatic activities. The functional specificities of these enzymes are at the current time poorly understood. The *Trichoderma reesei* genome comprises at least 3 main enzymes, derived from families 7 (EG1, cel7b), 5 (EG2, cel5a) and 12 (EG3, cel12a). The EG1 and EG2 enzymes are the major endoglucanases and can represent up to 10-20% by weight of the complete cocktail of enzymes produced by *T. reesei*.

Endoglucanases (EC 3.2.1.4), the first enzymes to act on cellulose, are known to have a major role in hydrolysis by increasing the number of sites that exoglucanases can attack, while decreasing the degree of polymerization of the microfibrils attacked. Recent studies (Szijártó, N., Siika-aho, M., Sontag-Strohm, T., & Viikari, L. (2011). Liquefaction of hydrothermally pretreated wheat straw at high-solids content by purified *Trichoderma* enzymes. *Bioresource technology*, 102(2), 1968-74) emphasize their role in decreasing the viscosity of the biomass during the first hours of hydrolysis. This decrease in viscosity can have a very significant impact on the operating costs of the process.

The viscosity problem is exacerbated in the case of processes which necessitate recourse to a low temperature, such as simultaneous saccharification and fermentation (SSF), which involves both the enzymes which hydrolyze the biomass and the microorganism which converts the sugar monomers to ethanol.

The hydrolysis and the fermentation can be carried out according to various schemes. The most common consists of separate hydrolysis and fermentation (SHF). This method makes it possible to optimize each step by maintaining the optimal reaction conditions. This fermentation is carried out extemporaneously, at a temperature of between approximately 28° C. and approximately 30° C., while the hydrolysis generally takes place at a temperature of at least 45° C. However, in SHF, the sugars released at the end of the reaction are present at very high concentration and lead to inhibition of the enzymes, slowing down the efficiency of the process. In order to avoid these drawbacks, another type of process can be envisioned. In SSF, the two steps (hydrolysis and fermentation of the hexoses) are carried out simultaneously, preventing accumulation of the sugars at concentrations that are inhibitory for the enzymes. The investment costs are also reduced by virtue of the use of a single reactor. The degree of hydrolysis is higher following the absence of inhibition since the sugars released are used immediately for the fermentation to ethanol. In this method, the reactor temperature necessarily constitutes a compromise between the optimal temperatures for hydrolysis and for fermentation, typically between approximately 30° C. and approximately 35° C. However, at such a temperature, the activity of the cellulolytic enzymes is decreased by approximately 30%.

SSF also allows the expression of enzymes that break down cellulose in the organism fermenting the sugars, thereby making it possible to limit, or in an extreme case eliminate, recourse to enzymes produced during a separate step. However, producing large amounts of enzymes with fermentative organisms and therefore obtaining a high activity can prove to be problematic and limits the viability of these approaches.

Consequently, the obtaining of enzymes which maintain an effective endoglucanase activity at the optimal temperatures for hydrolysis and for fermentation (i.e. between 30° C. and 50° C.) while at the same time keeping the proportion of all the enzymes of the mixture would be a significant gain for the process of converting lignocellulosic biomass to biofuel.

DESCRIPTION OF THE INVENTION

The inventors have developed a polypeptide having an improved endoglucanase activity, in particular compared with the endoglucanase activity of the wild-type EG1 protein of sequence SEQ ID NO: 2. EG1 corresponds to *Trichoderma reesei* endoglucanase 1.

With this perspective, the applicants have to their great credit found, after numerous research studies, an isolated or purified polypeptide having an improved endoglucanase activity compared with the endoglucanase activity of the EG1 reference protein (SEQ ID NO: 2).

The invention therefore relates to a polypeptide chosen from the group consisting of:
i) an amino acid sequence chosen from SEQ ID NO: 4, SEQ ID NO: 6, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24 and SEQ ID NO: 26;
ii) an amino acid sequence having a percentage identity of at least 70%, preferentially of 75%, 80%, 85%, 90%, 95%, 98% or 99%, relative to the sequence SEQ ID NO: 4, SEQ ID NO: 6, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24 or SEQ ID NO: 26.

Preferably, the polypeptide as described above is characterized in that its expression in a fermentative organism is at least equal to the expression of the EG1 reference protein (SEQ ID NO: 2).

According to the invention, the percentage identity of a given sequence relative to SEQ ID NO: 4, 6, 8, 10, 12, 14, 16, 18, 20, 22, 24 or 26 corresponds to the number of residues that are identical between this given sequence and SEQ ID NO: 4, 6, 8, 10, 12, 14, 16, 18, 20, 22, 24 or 26 divided by the number of residues in SEQ ID NO: 4, 6, 8, 10, 12, 14, 16, 18, 20, 22, 24 or 26. When the GenomeQuest database is used, said percentage identity relative to SEQ ID NO: 4, 6, 8, 10, 12, 14, 16, 18, 20, 22, 24 or 26 corresponds to the Query percentage identity (% id Query), where Query corresponds to the sequence SEQ ID NO: 4, 6, 8, 10, 12, 14, 16, 18, 20, 22, 24 or 26.

Those skilled in the art will be able, for example, to determine the increase or in other words the improvement in the enzymatic activity either using the substrate carboxymethylcellulose (CMC), or with a chromogenic substrate (p-nitrophenyl glycoside). The enzymatic activity will be respectively revealed by colorimetric assay of the reducing sugars or else of the nitrophenol released.

Preferably, the polypeptide of the invention has an enzymatic activity improved by at least 10%, preferentially by at least 20%, preferentially by at least 30%, relative to the endoglucanase activity of the EG1 protein of amino acid sequence SEQ ID NO: 2.

An example of a protocol, that those skilled in the art will be able to use to determine whether a polypeptide according to the invention has an improved enzymatic activity relative to that of the EG1 reference protein (SEQ ID NO: 2) is the following:
formation of a stock culture of *E. coli* expressing a polypeptide according to the invention overnight at 37° C.;
inoculation of an LB culture medium with 1% of stock culture at 37° C. until an optical density of 0.4 is obtained;
culture of said cells at 20° C. for 18 h;
centrifugation for 5 minutes at 7900 rpm;
resuspension of the cell pellets with 100 mM citrate phosphate buffer at pH 5 containing 1 mg/ml of lysozyme (final $OD_{600}$ 100);
incubation of the resuspended cells for 30 minutes on ice;
lysis of the cells by means of 3 cycles of freezing/thawing;
fractionation of the DNA by sonication;
centrifugation for 30 minutes at 13000 rpm;
incubation of 100 µl of breaking supernatant with 100 µl of 100 mM citrate phosphate buffer at pH 5 containing 1% of CMC for 6 h at 35 and 50° C.;
removal of 100 µl of reaction;
addition of 100 µl of DNS reagent (Miller, 1959);
incubation for 5 minutes at 100° C.;
incubation for 3 minutes on ice;
centrifugation for 10 minutes at 3000 rpm;
reading of the optical density at 540 nm on 150 µl of supernatant.

A subject of the invention is also a purified or isolated nucleic acid encoding at least one polypeptide as described above. Table 1 below comprises the identifications of the nucleic and peptide sequences for *T. reesei* EG1 ("wild-type"), the putative endoglucanases of *Chaetomium globosum* (C) and of *Aspergillus fumigatus* (A), and also for the polypeptides and nucleotides of the invention.

Preferably, said purified or isolated nucleic acid can be chosen from the following sequences: SEQ ID NO: 3, SEQ ID NO: 5, SEQ ID NO: 7, SEQ ID NO: 9, SEQ ID NO: 11; SEQ ID NO: 13, SEQ ID NO: 15, SEQ ID NO: 17, SEQ ID NO: 19, SEQ ID NO: 21, SEQ ID NO: 23 and SEQ ID NO: 25.

TABLE 1

| Clones | Nucleic acid | Polypeptide |
| --- | --- | --- |
| EG1 (wild-type) | SEQ ID NO: 1 | SEQ ID NO: 2 |
| 76B4 | SEQ ID NO: 3 | SEQ ID NO: 4 |
| 105F11 | SEQ ID NO: 5 | SEQ ID NO: 6 |
| 107H12 | SEQ ID NO: 7 | SEQ ID NO: 8 |
| 154E4 | SEQ ID NO: 9 | SEQ ID NO: 10 |
| 202C12 | SEQ ID NO: 11 | SEQ ID NO: 12 |
| 272A9 | SEQ ID NO: 13 | SEQ ID NO: 14 |
| 278F10 | SEQ ID NO: 15 | SEQ ID NO: 16 |
| 293B2 | SEQ ID NO: 17 | SEQ ID NO: 18 |
| 309A11 | SEQ ID NO: 19 | SEQ ID NO: 20 |
| 11G8 | SEQ ID NO: 21 | SEQ ID NO: 22 |

TABLE 1-continued

| Clones | Nucleic acid | Polypeptide |
| --- | --- | --- |
| 92A12 | SEQ ID NO: 23 | SEQ ID NO: 24 |
| 240H12 | SEQ ID NO: 25 | SEQ ID NO: 26 |
| Gene C | SEQ ID NO: 27 | SEQ ID NO: 28 |
| Gene A | SEQ ID NO: 29 | SEQ ID NO: 30 |

The invention also relates to a vector comprising a nucleic acid as described above.

According to the invention, the term "vector" is intended to mean any DNA sequence into which it is possible to insert fragments of foreign nucleic acid, the vectors making it possible to introduce foreign DNA into a host cell. As vectors, mention may be made, nonexhaustively, of: plasmids, cosmids, yeast artificial chromosomes (YACs), bacterial artificial chromosomes (BACs), P1 bacteriophage-derived artificial chromosomes (PACs) or virus-derived vectors.

According to the invention, the nucleic acid as described above may be functionally linked to a promoter, a terminator or any other sequence required for its expression in the host cell.

The vector according to the invention may also carry a selectable marker. The term "selectable marker" is intended to mean a gene of which the expression confers on the cells that contain it a characteristic which makes it possible to select them. It is, for example, a gene for resistance to antibiotics.

A subject of the invention is also an isolated host cell comprising either at least one of the polypeptides as described above, or at least one of the nucleic acids as described above or at least one of the vectors as described above.

Those skilled in the art will be able to introduce one of the polypeptides, one of the nucleic acids or one of the vectors as described above into the host cell by means of well-known conventional methods. For example, mention may be made of treatment with calcium chloride, electroporation, or the use of a particle gun.

According to one embodiment, those skilled in the art will be able to introduce into the host cell, and by means of conventional methods, several copies of a nucleic acid encoding a polypeptide having an improved endoglucanase activity according to the invention.

According to one embodiment, the isolated host cell as described above is chosen from *Trichoderma, Aspergillus, Neurospora, Humicola, Myceliophthora, Chrysosporium, Penicillium, Fusarium, Thermomonospora, Bacillus, Pseudomonas, Escherichia, Clostridium, Cellulomonas, Streptomyces, Yarrowia, Pichia* and *Saccharomyces*.

According to one preferred embodiment, the isolated host cell as described above is chosen from *Trichoderma reesei, Trichoderma viridae, Trichoderma koningii, Aspergillus niger, Aspergillus nidulans, Aspergillus wentii, Aspergillus oryzae, Aspergillus phoenicis, Myceliophthora thermopila, Chrysosporium lucknowense, Neurospora crassa, Humicola grisae, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae*.

According to one preferred embodiment, the isolated host cell as described above is chosen from *Trichoderma reesei* and *Saccharomyces cerevisiae*.

A subject of the invention is also the use of any one of the polypeptides described above, for the hydrolysis of cellulose.

A subject of the invention is also the use of any one of the polypeptides described above, for the production of biofuel.

According to the invention, the term "biofuel" can be defined as being any product resulting from the conversion of biomass and which can be used for energy purposes. Furthermore and without wishing to be limited, mention may be made, by way of example, of biogases, products which can be incorporated (optionally after subsequent conversion) into a fuel or may be a fuel in its own right, such as alcohols (ethanol, butanol and/or isopropanol depending on the type of fermentative organism used), solvents (acetone), acids (butyric acid), lipids and derivatives thereof (short-chain or long-chain fatty acids, fatty acid esters), and also hydrogen.

Preferably, the biofuel according to the invention is an alcohol, for example ethanol, butanol and/or isopropanol. More preferentially, the biofuel according to the invention is ethanol.

In another embodiment, the biofuel is biogas.

In another embodiment, the product is a molecule of interest to the chemical industry, for instance another alcohol such as 1,2-propanediol, 1,3-propanediol, 1,4-butanediol, 2,3-butanediol, organic acids such as acetic acid, propionic acid, acrylic acid, butyric acid, succinic acid, malic acid, fumaric acid, citric acid or itaconic acid, or hydroxy acids such as glycolic acid, hydroxypropionic acid or lactic acid.

Described below is an embodiment of production of an enzymatic cocktail that is useful for the hydrolysis of lignocellulose.

The strains of filamentous fungi, preferably *Trichoderma*, more preferentially *T. reesei*, capable of expressing at least one polypeptide according to the invention are cultured in fermentors, in the presence of a carbon-based substrate, such as lactose or glucose, chosen for growth of the microorganism. In one embodiment, this carbon-based substrate, depending on its nature, is introduced into the fermentor before sterilization or is sterilized separately and introduced into the fermentor after sterilization of the latter so as to obtain an initial concentration of 20 to 35 g/l.

An aqueous solution containing the substrate chosen for the production of the enzymes is then added. An enzymatic composition which acts on the lignocellulosic biomass produced by the fungi is finally recovered by filtration of the culture medium. In this composition are, in particular, the β-glucosidase, the exoglucanase and the endoglucanase according to the invention.

In one embodiment, the aqueous solution containing the substrate chosen for the production of the enzymes is prepared at the concentration of 200-250 g/l. This solution also preferably contains an inducer substrate such as lactose. This aqueous solution is injected after the exhaustion of the initial carbon-based substrate so as to provide an optimized amount of between 35 and 45 mg/g of cells ("fed batch"). During this "fed batch" phase, the residual concentration of sugar in the culture medium is less than 1 g/l and the enzymes which act on the lignocellulosic biomass are secreted by the fungus. The latter can be recovered by filtration of the culture medium.

A subject of the invention is an enzymatic composition capable of acting on lignocellulosic biomass, said enzymatic composition being produced by filamentous fungi and comprising at least one polypeptide having improved endoglucanase activity relative to the endoglucanase activity of the EG1 reference protein. The term "filamentous fungi" is intended to mean in particular *Trichoderma*, more preferentially *T. reesei*.

Finally, a subject of the invention is a process for producing biofuel from biomass, comprising the following successive steps:
- suspension, in an aqueous phase, of the biomass to be hydrolyzed;
- hydrolysis, in the presence of an enzymatic composition, of the lignocellulosic biomass as described above so as to produce a hydrolysate containing glucose;
- fermentation of the glucose of the hydrolysate so as to produce a fermentation must;
- separation of the biofuel from the fermentation must.

In one embodiment, the biomass to be hydrolyzed is suspended in an aqueous phase in a proportion of from 6% to 40% of solids, preferably 20% to 30%. The pH is adjusted to between 4 and 5.5; preferably, between 4.8 and 5.2, and the temperature is adjusted to between 40 and 60° C., preferably between 45 and 50° C. The hydrolysis reaction is initiated by adding the enzymatic composition which acts on lignocellulosic biomass; the amount normally used is from 10 to 30 mg of excreted proteins per gram of pretreated substrate or less. The reaction generally lasts from 15 to 48 hours. The reaction is monitored by assaying the sugars released, in particular glucose. The solution of sugars is separated from the nonhydrolyzed solid fraction, essentially consisting of lignin, by filtration or centrifugation and subsequently treated in a fermentation unit.

After the fermentation step, the biofuel is separated from the fermentation must for example by distillation.

Another subject of the invention is a process for producing biofuel from biomass, characterized in that it comprises the following successive steps:
- suspension, in an aqueous phase, of the biomass to be hydrolyzed;
- simultaneous addition of an enzymatic composition as defined above and of a fermentative organism so as to produce a fermentation must;
- separation of the biofuel from the fermentation must.

Preferably, the enzymatic composition and the fermentative organism are added simultaneously and then incubated in a temperature of between 30° C. and 35° C. so as to produce a fermentation must.

According to this embodiment, the cellulose present in the biomass is converted to glucose, and at the same time, in the same reactor, the fermentative organism (for example a yeast) converts the glucose to final product according to an SSF (Simultaneous Saccharification and Fermentation) process known to those skilled in the art. Depending on the metabolic and hydrolytic capacities of the fermentative organism, a more or less large amount of exogenous cellulolytic mixture may need to be added in order for the operation to proceed correctly.

In another embodiment, the fermentative organism produces the polypeptide which is the subject of the invention by secretion or at the surface of its cell, optionally together with other enzymes which act on lignocellulosic biomass, thus limiting or eliminating the need for enzymes produced by the filamentous fungus. Preferably, the fermentative organism is a host cell as described above.

Thus, preferably, a subject of the invention is a process for producing biofuel from biomass, comprising the following successive steps:
- suspension, in an aqueous phase, of the biomass to be hydrolyzed;
- addition of one or more host cells as described above, with a fermentative organism and/or an enzymatic composition as described above, so as to produce a fermentation must;
- separation of the biofuel from the fermentation must.

Preferably, the host cells with the enzymatic composition and/or the fermentative organism are added and then incubated at a temperature of between 30° C. and 35° C. so as to produce a fermentation must.

The use of the polypeptide having an improved endoglucanase activity according to the present invention thus has the advantage of obtaining a better glucose production yield while employing less enzyme than previously, which also provides an economic advantage.

Other aspects, subjects, advantages and characteristics of the invention will be presented on reading the nonrestrictive description which follows and which describes preferred embodiments of the invention, given by means of examples and of the figures.

EXAMPLES

Example 1

$1^{st}$ Round of L-shuffling

Figure 1:
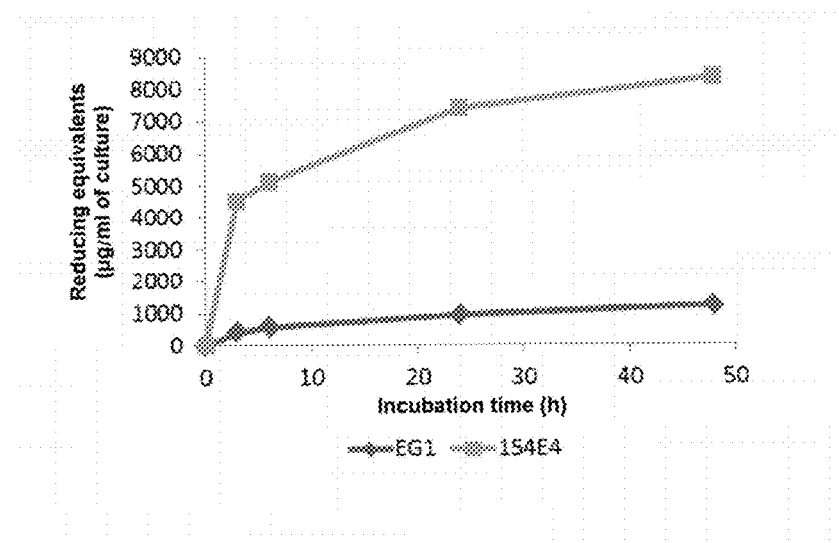
FIG. 1 is a graph representing the hydrolysis of 1% CMC by the reference endoglucanase (EG1) and its mutant (154E4) secreted into the culture medium by the strains Scα-EG1 and Scα-154E4, respectively.

The sequence of the *Trichoderma reesei* EG1 reference gene (SEQ ID NO: 1) was subjected to a first round of L-shuffling according to the process described in EP1104457B1 with the genes of the putative endoglucanase of *Chaetomium globosum* (SEQ ID NO: 29) and of the endoglucanase of *Aspergillus fumigatus* (SEQ ID NO: 27) each having approximately 60% identity with the reference gene SEQ ID NO: 1.

1—High-throughput Screening

A high-throughput screening test was developed in order to select the best clones resulting from the L-shuffling, i.e. those exhibiting at least 20% improvement in the endoglucanase activity relative to the reference enzyme SEQ ID NO: 2.

The high-throughput screening test was carried out according to the following steps:
- isolation on agar of the *E. coli* clones expressing the L-shuffling variants of the recombinant enzyme according to the invention and preculturing of said colonies in LB medium overnight at 37° C.;
- inoculation of an LB medium at 6% with the preculture, then incubation for 5 hours at 37° C., then 17 hours at 20° C.;
- centrifugation for 10 minutes at 3000 rpm;
- lysis of the cells by addition of 80 µl of a solution of lysozyme at 1 mg/ml in a 0.1 M citrate phosphate buffer at pH 5;
- incubation for 4 hours at ambient temperature;
- addition of 80 µl of 0.1 M citrate phosphate buffer, pH 5, containing 1% of carboxymethylcellulose;
- incubation for 17 hours at 35° C.;
- centrifugation for 10 minutes at 3000 rpm;
- removal of 100 µl of supernatant;
- addition of 100 µl of DNS reagent;
- incubation for 10 minutes at 100° C. and then 5 minutes on ice;
- reading of the OD at 540 nm on 120 µl.

Under these high-throughput screening conditions, an improvement in the endoglucanase activity (increase in the OD at 540 nm) relative to the EG1 reference enzyme (SEQ ID NO: 2) was found in several clones, including in particular the clones 76B4, 105F11, 107H12, 154E4, 202C12, 272A9, 278F10, 293B2 and 309A11.

2—Determination of the Improvement in the Endoglucanase Activity 2-1/On the Carboxymethylcellulose (CMC) Substrate In order to estimate the kcat of the variants selected in the first round of L-shuffling compared with the reference enzyme (SEQ ID NO: 2), the following procedure is carried out:
- preparation of a stock culture of *E. coli* expressing a recombinant enzyme according to the invention overnight at 37° C.;
- inoculation of an LB culture medium with 1% of stock culture at 37° C. until an optical density at 600 nm of 0.4 is obtained;
- culture of said cells at 20° C. for 18 hours;
- centrifugation for five minutes at 7900 rpm;
- resuspension of the cell pellets with 0.1 M citrate phosphate buffer at pH 5 containing 1 mg/ml of lysozyme (final $OD_{600}$ 100);
- incubation of the resuspended cells for 30 minutes on ice;
- lysis of the cells by means of 3 cycles of freezing/thawing;
- fractionation of the DNA by sonication for 3 seconds at power 5;
- centrifugation for 30 minutes at 13000 rpm;
- incubation of 100 µl of breaking supernatant with 100 µl of 0.1 M citrate phosphate buffer at pH 5 containing 1% of CMC for 6 hours at 35 and 50° C.;
- removal of 100 µl of reaction;
- addition of 100 µl of DNS reagent;
- incubation for 5 minutes at 100° C.;
- incubation for 3 minutes on ice;
- centrifugation for 10 minutes at 3000 rpm;
- reading of the optical density at 540 nm on 150 µl.

According to the invention, the kcat values are calculated in the following way:
- expressing the ODs at 540 nm as a function of the amount of protein of interest (in nM);
- subtracting the value of the negative control;
- dividing by the coefficient of the glucose standard range (various amounts of glucose are revealed with DNS)
- dividing by the reaction time (360 minutes).

Table 2 presents the kcat values and also the improvement factor obtained for the clones 76B4, 105F11, 107H12, 154E4, 202C12, 236C11, 272A9, 278F10, 293B2 and 309A11 relative to the EG1 reference protein (SEQ ID NO: 2) under the experimental conditions of the activity test on CMC.

TABLE 2

Endoglucanase activity on CMC

| | Clone | 35° C. | | 50° C. | |
| --- | --- | --- | --- | --- | --- |
| | | kcat (min$^{-1}$) | Improvement factor | Kcat (min$^{-1}$) | Improvement factor |
| First-round clones | 76B4 | 0.25 | 1 | 0.35 | 1.1 |
| | 105F11 | 1.13 | 4.7 | 1.24 | 4 |
| | 107H12 | 1.06 | 4.4 | 1.14 | 3.7 |
| | 154E4 | 1.27 | 5.3 | 3.39 | 10.9 |
| | 202C12 | 0.73 | 3 | 0.61 | 2 |
| | 236C11 | 0.12 | 5.3 | 0.05 | 0.2 |
| | 272A9 | 0.99 | 4.1 | 2.33 | 7.5 |
| | 278F10 | 0.95 | 4 | 1.06 | 3.4 |
| | 293B2 | 1.04 | 4.3 | 1.78 | 5.7 |
| | 309A11 | 1.07 | 4.5 | 0.6 | 1.9 |
| Reference protein | EG1 | 0.24 | 1 | 0.31 | 1 |

The results show, for these clones, an improvement in enzymatic activity relative to the reference enzyme SEQ ID NO: 2.

2-2/On the Phosphoric Acid Swollen Cellulose (PASC) Substrate

The improvement in activity of the clones 76B4, 105F11, 107H12, 154E4, 202C12, 236C11, 272A9, 278F10, 293B2 and 309A11 was then confirmed on a second substrate: phosphoric acid swollen cellulose (PASC).

The determination of the kcat on this substrate is carried out according to the same protocol as described above. The CMC substrate is replaced with the PASC substrate at the same concentration.

Table 3 presents the kcat values and also the improvement factor obtained for the clones 76B4, 105F11, 107H12, 154E4, 202C12, 236C11, 272A9, 278F10, 293B2 and 309A11 relative to the EG1 reference protein (SEQ ID NO: 2) under the experimental conditions of the activity test on PASC.

TABLE 3

Endoglucanase activity on PASC

| | Clone | 35° C. | | 50° C. | |
| --- | --- | --- | --- | --- | --- |
| | | kcat (min$^{-1}$) | Improvement factor | Kcat (min$^{-1}$) | Improvement factor |
| First-round clones | 76B4 | 0.0116 | 1.66 | 0.0127 | 1.81 |
| | 105F11 | 0.0099 | 1.41 | 0.0109 | 1.56 |
| | 107H12 | 0.0069 | 0.99 | 0.0068 | 0.97 |
| | 154E4 | 0.0101 | 1.44 | 0.0104 | 1.49 |

TABLE 3-continued

Endoglucanase activity on PASC

| | | 35° C. | | 50° C. | |
|---|---|---|---|---|---|
| | Clone | kcat (min$^{-1}$) | Improvement factor | Kcat (min$^{-1}$) | Improvement factor |
| | 202C12 | 0.0098 | 1.4 | 0.0097 | 1.39 |
| | 236C11 | 1.0102 | 1.46 | 0.0103 | 1.47 |
| | 272A9 | 0.0103 | 1.47 | 0.0099 | 1.41 |
| | 278F10 | 0.0094 | 1.34 | 0.0091 | 1.3 |
| | 293B2 | 0.0089 | 1.27 | 0.0088 | 1.26 |
| | 309A11 | 0.0102 | 1.46 | 0.0089 | 1.27 |
| Reference protein | EG1 | 0.007 | 1 | 0.007 | 1 |

These results show an improvement in the enzymatic activity relative to the EG1 reference enzyme (SEQ ID NO: 2).

Example 2

2nd Round of L-shuffling

The improved genes 105F11, 154E4, 202C12, 272A9, 278F10 and 309A10 (respectively SEQ ID NO: 5, 9, 11, 13, 15, 19) obtained in the first round of evolution was subsequently subjected to a second round of L-shuffling (still according to the patented process described in EP1104457B1). In order to promote reconstruction on a backbone of the *Trichoderma* sequence, the EG1 reference gene (SEQ ID NO: 1) was reintroduced as parent gene for the second round of L-shuffling.

1—High-throughput Screening

A high-throughput screening test as described above was carried out on the clones obtained following this second round of L-shuffling in order to select the best ones. The activity test was reduced to 2 hours (compared with 17 hours for the screening of the clones resulting from the first round of evolution) in order to take into account the improvements obtained with the first round of L-shuffling.

The activity of the clones generated is compared with the activity obtained with the clone 154E4. This clone, resulting from the first round of L-shuffling, is the one which made it possible to obtain the best improvement in activity.

Under these screening conditions, an improvement in the endoglucanase activity relative to the 154E4 reference clone (SEQ ID NO: 10) was found in several clones, including in particular the clones 11G8 and 240H12.

2—Determination of the Improvement in the Endoglucanase Activity 2-1/On the Carboxymethylcellulose (CMC) Substrate In order to determine the kcat, the activities of the clones 11G8, 92A12 and 240H12 were measured using the activity test as described above. The duration of the activity test was reduced to one hour of incubation with the substrate in order to take into account the improvements of these clones.

Table 4 presents the kcat values and also the improvement factor obtained for the clones 11G8, 92A12 and 240H12 relative to the 154E4 clone (SEQ ID NO: 10) under these experimental conditions.

TABLE 4

Endoglucanase activity on CMC

| | | 35° C. | | 50° C. | |
|---|---|---|---|---|---|
| | Clone | kcat (min$^{-1}$) | Improvement factor | Kcat (min$^{-1}$) | Improvement factor |
| Second-round clones | 11G8 | 804.7 | 1.8 | 944.2 | 1.9 |
| | 92A12 | 420 | 0.94 | 487.5 | 0.95 |
| | 240H12 | 488.6 | 1.1 | 590.8 | 1.2 |
| Reference protein | 154E4 | 446.4 | 1 | 501.3 | 1 |

The results show an improvement in activity relative to the 154E4 reference clone for the clones 11G8 and 240H12.

2-2/On the Phosphoric Acid Swollen Cellulose (PASC) Substrate

The improvement in activity of the clones 11G8, 92A12 and 240H12 was then confirmed on a second substrate: phosphoric acid swollen cellulose (PASC).

In order to determine the kcat, the activity of these clones was measured at 35 and 50° C. using the activity test as described above with PASC as substrate.

Table 5 presents the kcat values and also the improvement factor obtained for the clones 11G8, 92A12 and 240H12 relative to the clone 154E4 (SEQ ID NO: 10) under these experimental conditions.

TABLE 5

Endoglucanase activity on PASC

| | | 35° C. | | 50° C. | |
|---|---|---|---|---|---|
| | Clone | kcat (min$^{-1}$) | Improvement factor | Kcat (min$^{-1}$) | Improvement factor |
| Second-round clones | 11G8 | 1.37 | 0.8 | 1.72 | 1.1 |
| | 92A12 | 1.36 | 0.81 | 1.7 | 1.04 |
| | 240H12 | 1.87 | 1.1 | 1.9 | 1.2 |
| Reference protein | 154E4 | 1.68 | 1 | 1.63 | 1 |

The activity of the clone 11G8 is not improved at 35° C. on this substrate relative to the reference clone 154E4. On the other hand, the activity of the clone 11G8 is improved at 50° C. The activity of the clone 240H12 is improved at 35° C. and at 50° C.

Example 3

Cloning of an Endoglucanase 1 Variant Resulting from the First Round of L-shuffling in a *T. reesei* Strain CL847 ΔEG1

The construction of the DNA fragment to be inserted into *T. reesei*, containing the clone 154E4 resulting from the first round of the L-shuffling, was carried out by PCR fusion. The fragment approximately 5.4 kb in length consisted of the phleomycin resistance gene, and the coding sequence of the clone 154E4 under the control of the cbh1 promoter and followed by the cbh1 terminator. In the same way, the *T. reesei* EG1 reference gene (SEQ ID NO: 1) was amplified and fused between the cbh1 promoter and terminator, resulting in a second construct.

Protoplasts of a *T. reesei* strain CL847 ΔEG1 were transformed according to a conventional method known to those skilled in the art, by calcium and PEG shock, with 5 μg of each construct, namely the DNA fragment containing either the 154E4 gene or the EG1 gene. The transformants were selected on PDA/sucrose selective medium containing 30 μg/l of phleomycin. Fourteen clones from each transformation were subcultured. After three subculturings in order to isolate pure clones, seven clones having integrated the native gene and five clones having integrated the 154E4 variant and secreting a protein level comparable to the strain CL847 were finally obtained.

1—Screening Using an Activity Test on Carboxymethylcellulose (CMC)

The 11 clones were cultured in 24-well plates containing the following medium:
800 μl of 85% $H_3PO_4$ 85%, 4.2 g of $(NH_4)_2SO_4$, 0.3 g of $MgSO_4 \cdot 7H_2O$, 1.5 g of CornSteep, 1 ml of Oligo Ferment, 11.6 g of maleic acid, 10 g of Solka-Floc and 20 g of lactose per liter of medium. The pH is adjusted to 5.8-6.0. After 5 days of culture at 30° C., the supernatant is removed and the equivalent of 10 mg/l of proteins (measured by the Lowry method) is used for an activity test on CMC. 150 μl of a 2% CMC solution in 50 mM citrate buffer, pH 4.8, are mixed with 150 μl of citrate buffer containing 10 mg/l of proteins. The reaction is incubated at 50° C. or 35° C. for 10 minutes and then inactivated in a boiling water bath. After centrifugation for 5 minutes, 20 μl of supernatant are removed in order to assay reducing sugars using 3,5-dinitrosalicylic acid (DNS). The reduction of the DNS and the formation of 3-amino-5-nitrosalicylic acid are monitored by reading the absorption at 540 nm and the reducing sugars are quantified using a glucose range.

Table 6 summarizes the activities obtained with the clones containing the 154E4 variant, in comparison with the reference strain CL847, the strain CL847 ΔEG1, and the strain CL847 ΔEG1 retransformed with the EG1 reference gene (ΔEG1cEG1, average obtained with the best four transformants).

TABLE 6

Endoglucanase activity on CMC

| Clone | Specific activity 50° C. (μmol/mg/min) | 154E4/ ΔEG1cEG1 ratio (50° C.) | Specific activity 35° C. (μmol/mg/min) | 154E4/ ΔEG1cEG1 ratio (35° C.) |
|---|---|---|---|---|
| CL847 | 12.9 ± 3.1 | | 9.7 ± 0.4 | |
| ΔEG1 | 6.4 ± 0.4 | | — | |
| ΔEG1cEG1 | 16.8 ± 2.5 | | 12.1 ± 1.0 | |
| 154E4/2 | 22.5 ± 2.9 | 1.3 | 12.7 ± 2.0 | 1.1 |
| 154E4/8 | 24.1 ± 1.9 | 1.4 | 12.5 ± 2.0 | 1.0 |
| 154E4/9 | 20.2 ± 3.9 | 1.2 | 7.4 ± 2.2 | 0.6 |

The results show that the activities of the 154E4 variants are between 1.2 and 1.4 times greater than those of the clones retransformed with the EG1 reference gene (SEQ ID NO: 1). The improvement can be seen at 35° C. and at 50° C.

2—Cloning of the 11G8 Variant Obtained after the 2nd Round of L-shuffling in a *T. reesei* Strain CL847 ΔEG1 and Screening of the Transformants:

The 11G8 variant was cloned between the cbh1 promoter and terminator in the pUT1040 plasmid containing a phleomycin resistance gene as marker, by means of a BamH1/XhoI double digestion. 5 μg of this vector were used to transform the *T. reesei* strain CL847 ΔEG1. The transformation of the protoplasts was carried out under the same conditions as for the 154E4 variant. At the end of the transformation process and of three successive subculturings carried out for the purpose of obtaining pure clones, thirteen clones with a protein production similar to the CL847 strain were obtained and were subjected to the screening by measuring CMCase activity. The activity test is identical to the screening of the clones containing the 154E4 variant from the first round of L-shuffling. Six clones expressing the 11G8 variant show a CMCase activity that is greater than that of the ΔEG1cEG strain. The best two transformants have an activity increased by 70% compared with the strain expressing the EG1 reference gene (SEQ ID NO: 1).

Table 7 summarizes the activities obtained with the clones containing the 11G8 variant, in comparison with the CL847 reference strain, the CL847 ΔEG1 strain and the CL847 ΔEG1 strain retransformed with the EG1 reference gene (ΔEG1cEG1, average obtained with the best four transformants).

TABLE 7

Endoglucanase activity on CMC

| Clone | Specific activity 50° C. (μmol/mg/min) | 11G8/ΔEG1 cEG1 ratio (50° C.) | Specific activity 35° C. (μmol/mg/min) | 11G8/ ΔEG1cEG1 ratio (35° C.) |
|---|---|---|---|---|
| CL847 | 20.8 ± 0.8 | | 11.8 ± 0.5 | |
| ΔEG1 | — | | 3.3 ± 1.1 | |
| ΔEG1cEG1 | 13.2 ± 2.2 | | 9.1 ± 0.7 | |
| 11G8/6 | 15.6 ± 1.8 | 1.2 | 10.0 ± 0.4 | 1.1 |
| 11G8/7 | 17.3 ± 0.7 | 1.3 | 10.8 ± 0.9 | 1.2 |
| 11G8/9 | 17.9 ± 0.4 | 1.4 | 11.9 ± 0.2 | 1.3 |
| 11G8/10 | 15.0 ± 0.3 | 1.1 | 13.9 ± 1.6 | 1.5 |
| 11G8/12 | 17.0 ± 0.1 | 1.3 | 15.7 ± 0.8 | 1.7 |
| 11G8/13 | 17.3 ± 1.2 | 1.3 | 15.6 ± 0.4 | 1.7 |

The results show that the activities of the 11G8 variants are between 1.1 and 1.7 times greater than those of the clones retransformed with the reference gene SEQ ID NO: 1. The improvement can be seen at 35° C. and at 50° C.

Example 4

Recombinant Expression of the EG1 Reference Endoglucanase and of the 154E4 Improved Variant in *Saccharomyces cerevisiae*

1—Production of the Reference EG1 and 154E4 Proteins in the Extracellular Medium The endoglucanase genes of *Trichoderma reesei* (EG1) and of the 154E4 variant were cloned, without their signal peptide, into the pESC-LeuaAmyc vector (CNRS-CER-MAV). This construct allows the expression of the proteins in the culture medium of the *Saccharomyces cerevisiae* strain EBY100, which is auxotrophic for leucine and tryptophan (Boder E T and Wittrup K D, Biotechnol Prog, 1998, 14:55-62). This plasmid makes it possible to place the expression of the genes under the control of the galactose-inducible GAL1 promoter and possesses the auxotrophy selectable marker gene (Leu2) which allows the selection of the transformants.

The transformation of *Saccharomyces cerevisiae* EBY100 was carried out according to the conventional methods known to those skilled in the art (transformation of yeasts by heat shock and lithium acetate). The transformants were selected on 0.67% YNB-2% Glc-0.01% Trp medium.

One transformant for each gene (Scα-EG1 and Scα-154E4) was used to inoculate 15 ml of a 0.67% YNB-2% Glc-SD-0.01% Trp minimum medium. SD is a mixture of amino acids (40 mg/l of adenine sulfate; 20 mg/l of L-arginine; 100 mg/l of aspartic acid; 100 mg/l of L-glutamic acid; 20 mg/l of L-histidine; 30 mg/l of L-lysine; 20 mg/l of L-methionine; 50 mg/l of L-phenylalanine; 375 mg/l of L-serine; 200 mg/l of L-threonine; 30 mg/l of L-tyrosine; 150 mg/l of L-valine and 20 mg/l of uracil). After 24 hours of preculture at 30° C. with shaking at 220 rpm, the two strains of Scα-EG1 and Scα-154E4 were used to inoculate (OD$_{600}$ of 0.5) 150 ml of 0.67% YNB-2% Gal-SD-0.01% Trp medium. The cultures were incubated at 25° C. with shaking at 220 rpm. After 8 hours of incubation, 6 ml of sodium citrate at pH 5.6 were added to each culture in order to stabilize the pH at 5.

After 4 days of incubation, 20 ml of culture were removed. The culture supernatant was obtained after centrifugation at 3000 g, at 4° C., for 5 minutes.

2—Determination of the Endoglucanase Activity on p-nitrophenyl-β-lactoside

The endoglucanase activity of the culture supernatants was measured by hydrolysis of the p-nitrophenyl-β-lactoside (pNPL) substrate in a volume of 700 µl under the following conditions:

50 mM of citrate buffer at pH 5;
  2 mM of pNPL;
  605 µl and 90 µl of culture supernatant from the Scα-154E4 strains;
  incubation at 35° C. or 50° C. for 30 min for the Scα-EG1 strain.

The reaction was stopped by adding 100 µl of 1 M of sodium carbonate to 100 µl of the reaction medium. The concentration of para-nitrophenol (pNP) released by hydrolysis of pNPL was determined by measuring the absorbance at 415 nm by comparison with a para-nitrophenol standard range (linear from 0.36 µM to 360 µM).

Table 8 presents the results of endoglucanase activity (EA in nmol·min$^{-1}$·mL$^{-1}$ of culture) on pNPL at 35° C. and 50° C. of the culture media of the ScαEG1 and Scα154E4 strains.

TABLE 8

Endoglucanase activity on pNPL at 35° C. and 50° C. of the culture media of the ScαEG1 and Scα154E4 strains.

| | EA at 35° C. | EA at 50° C. | 35° C./50° C. Activity ratio | Improvement in EA at 35° C. |
|---|---|---|---|---|
| Scα-EG1 | 1.17 | 1.18 | 1 | — |
| Scα-154E4 | 45.0 | 61.1 | 1.4 | 38.5 |

The results obtained show an improvement at 35° C. in the enzymatic activity of the Scα-154E4 strain by a factor close to 40 relative to the strain expressing the *T. reesei* EG1 reference protein (SEQ ID NO: 2). The magnitude of the improvement in activity noted compared with *E. coli* and *T. reesei* suggests that the enzyme not only has an improved specific activity, but that it is also overexpressed and/or better secreted.

3—Determination of the Endoglucanase Activity on Carboxymethylcellulose

The endoglucanase activity of the culture supernatants was measured by hydrolysis of carboxymethylcellulose (CMC) in a volume of 700 µl under the following conditions:

50 mM of citrate buffer at pH 5;
  1% of CMC;
  210 µl of culture supernatant of the Scα-EG1 and Scα-154E4 strains respectively dialyzed against 50 mM citrate buffer, pH 5, on a 10 kDa membrane, and concentrated 2-fold;
  incubation at 35° C. for 48 hours.

The reaction was stopped by adding 150 µl of DNS reagent to 100 µl of the reaction medium. After heating for 5 minutes at 100° C. and cooling in ice, the amount of reducing sugars released was determined by measuring the absorbance at 550 nm by comparison with a standard range produced with glucose.

FIG. 1 presents the results of hydrolysis of the 1% CMC by the EG1 reference endoglucanase (SEQ ID NO: 2) and its mutant 154E4 (SEQ ID NO: 10) respectively secreted into the culture medium of the Scα-EG1 and Scα-154E4 strains.

The results of FIG. 1 show that, during the first hours of reaction, the amount of reducing sugars released per 1 ml of culture of the Scα-154E4 strain is approximately 10 times greater than with 1 ml of Scα-EG1. The magnitude of the improvement in activity noted compared with *E. coli* and *T. reesei* suggests that the enzyme not only has an improved specific activity, but that it is also overexpressed and/or better secreted.

Example 5

Production of Enzymes by *T. reesei* in Fed Flasks

The reference strains and those having the best activity on CMC (CL847, ΔEG1, ΔEG1cEG1, 154E4/2, 154E4/8, 11G8/10, 11G8/12, 11G8/13) were cultured in 250 ml Erlenmeyer flasks. 55 ml of F45 medium (10 g/l of dipotassiumphthalate buffer, pH 6, 4.2 g/l (NH$_4$)$_2$SO$_4$, 300 mg/l MgSO$_4$.7H$_2$O, 150 mg/l CaCl$_2$.2H$_2$O, 1.5 g/l cornsteep, 0.07% orthophosphoric acid, 5 mg/l FeSO$_4$, 1.4 mg/l MnSO$_4$, 1.4 mg/l ZnSO$_4$, 3.7 mg/l CoCl$_2$ and 12.5 g/l glucose) are inoculated and shaken at 150 rpm and 30° C. The enzyme production is carried out in two phases: a batch phase on glucose and a fed-batch phase on lactose. Regular samples make it possible to determine the moment in which the glucose concentration goes below 3 g/l. At this stage, fed-batch feeding using a syringe driver (6-way) is initiated. The cultures are fed with a solution of 50 g/l lactose and 0.3% NH$_3$ at a flow rate of 40 mg of sugar/g of biomass per hour. Daily samples are taken in order to determine the pH, the dry weight and the concentration of proteins in the supernatant. After 5 days of fed-batch culture, the culture is filtered through a 0.45 µm filter and the supernatant is frozen.

The final concentration of proteins was about 3 to 4 g/l. If the concentration was below 3 g/l, the supernatants were concentrated on a column (Vivaspin MWCO5, Sartorius).

Example 6

Effectiveness of the Enzymes Resulting from the L-shuffling in Hydrolysis of Lignocellulosic Biomass According to an SHF Process The reference substrate used is a wheat straw which has undergone a vapor-explosion pretreatment (19 bar-3 minutes) after acid impregnation with 0.01% of H$_2$SO$_4$ for 10 hours, and being washed, neutralized at pH 5, pressed and dried. Table 9 presents the composition of the reference substrate.

TABLE 9

Composition of the straw used for the hydrolysis tests

| Composition | % w/w |
|---|---|
| WIS | 97.52 |
| Ash content | 5 |
| Cellulose | 51.7 |
| Corrected xylans | 3.57 |
| Hemicellulose | 4.14 |
| Klason lignin (overestimated) | 36.49 |
| Acetyl | 0.6 |

The hydrolyses were carried out at 10% of solids w/w, i.e. an equivalent of 5.4% of cellulose w/w. The protein content is fixed at 10 mg/g of solids, i.e. approximately 19 mg/g of cellulose. The concentration of the enzymatic cocktails was measured by the Lowry method using BSA as reference. Each cocktail was supplemented with β-glucosidase activity in an amount of 120±2 IU/g of cellulose, by adding SP188 β-glucosidase (Novozymes).

The tests are carried out in Eppendorf tubes having a 2 ml working capacity (1 g reaction capacity) containing:
  0.11±0.001 g of washed straw substrate,
  0.9±0.02 ml of hydrolysis reaction medium composed of 50 mM acetate buffer, pH 4.8, and chloramphenicol (0.05 g/l),
  between 0.1 and 0.2±0.02 g of enzymatic cocktail depending on their protein content.

The enzymatic hydrolyses are carried out at 45±2° C. with vortex stirring at 900 revolutions per minute in an Eppendorf Thermomixer Comfort.

All the tests are carried out in duplicate with sampling times fixed at t 24, 48 and 96 hours with, for some, samples taken at t 72 hours.

At each sampling time, the hydrolysates are boiled for 5 minutes in the sacrificed Eppendorf tubes. These tubes are then cooled and centrifuged. The glucose assay is performed by HPLC. In parallel, the solid residues of each Eppendorf tube are washed and centrifuged 3 times before being dried at 105° C. for 24 hours so as to evaluate the WIS (Water Insoluble Solids). The hydrolysis yield is calculated taking into account the WIS.

The cocktails resulting from example 5 were evaluated. Two control tests are carried out with the reference cocktails also supplemented with β-glucosidase for comparison: a cocktail produced by the strain CL847 ΔEG1 (ΔEG1) and a cocktail produced by the strain CL847 ΔEG1 retransformed with the EG1 reference gene (ΔEG1cEG1).

Figure 2:
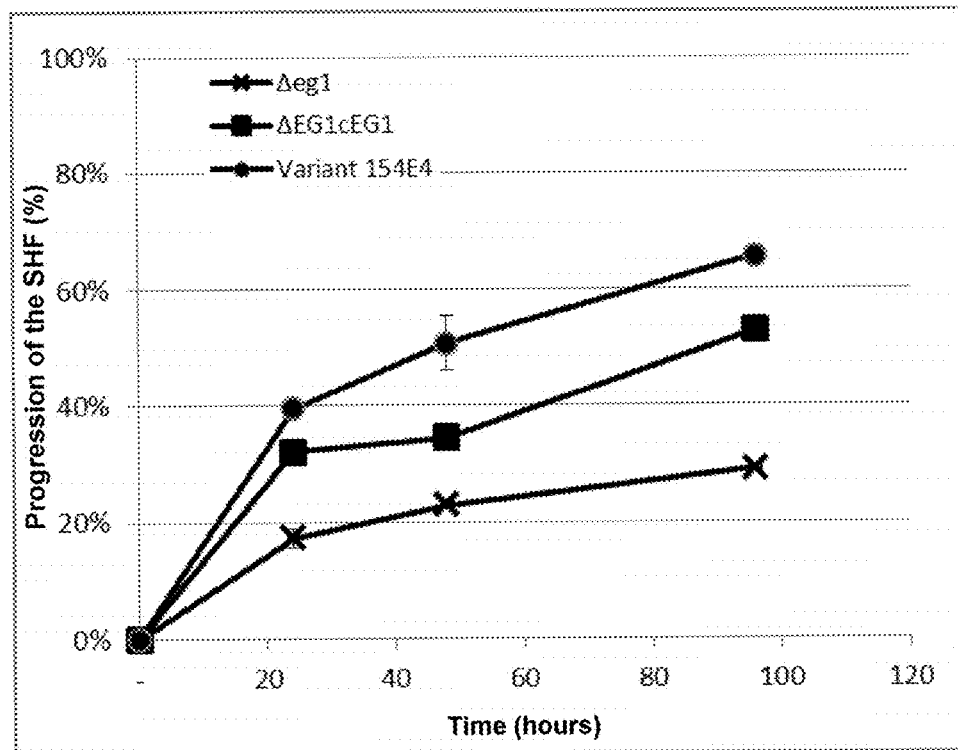
FIG. 2 is a graph presenting the results of SHF for the cocktail derived from the strain 154E4/8 (SEQ ID NO: 10), a reference cocktail produced by the strain CL847 ΔEG1 (ΔEG1) supplemented with β-glucosidase and another reference cocktail produced by the strain CL847 ΔEG1 retransformed with the EG1 reference gene (ΔEG1cEG1) supplemented with β-glucosidase.

FIG. 2 presents the results of SHF for the cocktail resulting from the strain 154/8 expressing the 154E4 variant (SEQ ID NO: 10).

The results presented in FIG. 2 show that the initial rate of hydrolysis of the cocktail produced by the 154E4 variant is greater than those of the ΔEG1 and ΔEG1cEG1 reference cocktails. The final hydrolysis yield is also greater than that of the ΔEG1 and ΔEG1cEG1 reference cocktails.

Figure 3:
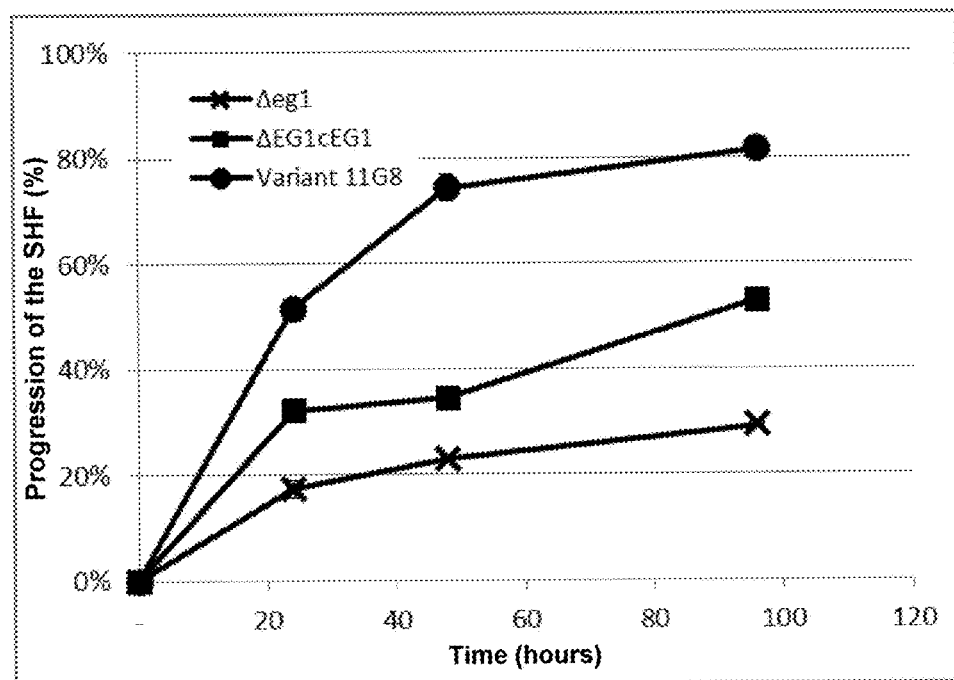
FIG. 3 is a graph presenting the results of SHF for the cocktail derived from the strain 11G8/10 (SEQ ID NO: 22), a reference cocktail produced by the strain CL847 ΔEG1 (ΔEG1) supplemented with β-glucosidase and another reference cocktail produced by the strain CL847 ΔEG1 retransformed with the EG1 reference gene (ΔEG1cEG1) supplemented with β-glucosidase.

FIG. 3 presents the results of SHF for the cocktail resulting from the strain 11G8/10 expressing the 11G8 variant (SEQ ID NO: 22).

The results presented in FIG. 3 show that the initial rate of hydrolysis of the cocktail produced by the 11G8 variant is greater than those of the ΔEG1 and ΔEG1cEG1 reference cocktails. The final hydrolysis yield is also greater than that of the ΔEG1 and ΔEG1cEG1 reference cocktails.

Example 7

Effectiveness of the Enzymes in Hydrolysis of Lignocellulosic Biomass According to an SSF Process The substrate used is the same as that described in table 9 (example 6).

The SSFs are carried out in triplicate in laboratory reactors. Said reactors consist of the following elements:
  a glass flask having a 30 ml working capacity;
  a polyether ether ketone (PEEK) safety stopper;
  a DV-118 one-way valve sold by the company Vaplock attached through the stopper. The valve is configured to open at the outlet when the relative pressure in the flask is greater than 70 mbar;
  a hollow polypropylene tube, fitted through a second, which passes through the stopper, and equipped at the lower end of said tube with a septum;
  a flat seal disposed between the neck of the flask and the stopper.

The principle for operating the bioreactors is the following: the $CO_2$ produced during the ethanolic fermentation accumulates in the top space located above the reaction medium, causing, by accumulation, an increase in the pressure in the bioreactor ($P_G$). When $P_G$ becomes greater than the pressure for opening the one-way valve ($P_S$), said valve opens to allow an amount of gas to escape, said amount being, for example, determined by weighing. When $P_G < P_S$, the valve closes again until $P_G$ is greater than $P_S$. Thus, the bioreactor when operating is always under pressure so as to ensure a stable anaerobic medium for the fermentation. The amount of ethanol produced is evaluated by the $CO_2$ production estimated by weight loss on the basis of the following stoichiometric equation for fermentation of glucose to ethanol:

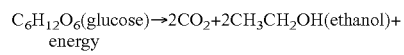

$$C_6H_{12}O_6(\text{glucose}) \rightarrow 2CO_2 + 2CH_3CH_2OH(\text{ethanol}) + \text{energy}$$

The culture medium used for the SSF is an aqueous medium which comprises:
  a 50 mM acetate buffer for pH 5;
  chloramphenicol at 0.1 g/l;
  nutritive medium containing 3 g/l of $KH_2PO_4$, 2 g/l of $(NH_4)_2SO_4$, 0.4 g/l of $MgSO_4.7H_2O$ and 1 g/l of yeast extract.

The SSFs were carried out at 10±0.01% w/w of solids, i.e. an equivalent of 5.4% cellulose w/w for a total reaction mass of 15±0.003 g. The protein content is fixed at 10±0.01 mg of cellulases per gram of solids, i.e. approximately 19 mg/g of cellulose. The concentration of the enzymatic cocktails was measured by the Lowry method using BSA (Bovine Serum Albumin) as reference. Each cocktail was supplemented with β-glucosidase activity in an amount of 120±2 IU/g of cellulose, by adding SP188 β-glucosidase (Novozymes).

The sugar fermentation yeast (*Saccharomyces cerevisiae*, Ethanol Red strain, Fermentis, France) is added to the medium so as to obtain a content of 2±0.1 g/kg.

The enzymes and the yeasts are added to the bioreactors after one hour of conditioning of the wheat straw that has been pretreated at 35° C. with the buffer, the chloramphenicol and the culture medium.

The SSF reaction is carried out at a temperature of approximately 35° C., by placing the laboratory bioreactor in an Infors HT Multitron Standard incubator with an orbital rotation speed of 150 revolutions per minute.

Over time, the weight loss was monitored by weighing the bioreactors. At the end of the reaction, the fermentation must is heated at 100° C. for 5 minutes, cooled and centrifuged in order to separate the non-hydrolyzed solids from the fermentation liquor. The latter is then analyzed by gas chromatography in order to determine its ethanol concentration.

The cocktails resulting from example 5 were evaluated. Two control tests are carried out with the reference cocktails also supplemented with β-glucosidase for comparison: a cocktail produced by the strain CL847 ΔEG1 (ΔEG1) and a cocktail produced by the strain CL847 ΔEG1 retransformed with the EG1 reference gene (ΔEG1cEG1).

Figure 4:
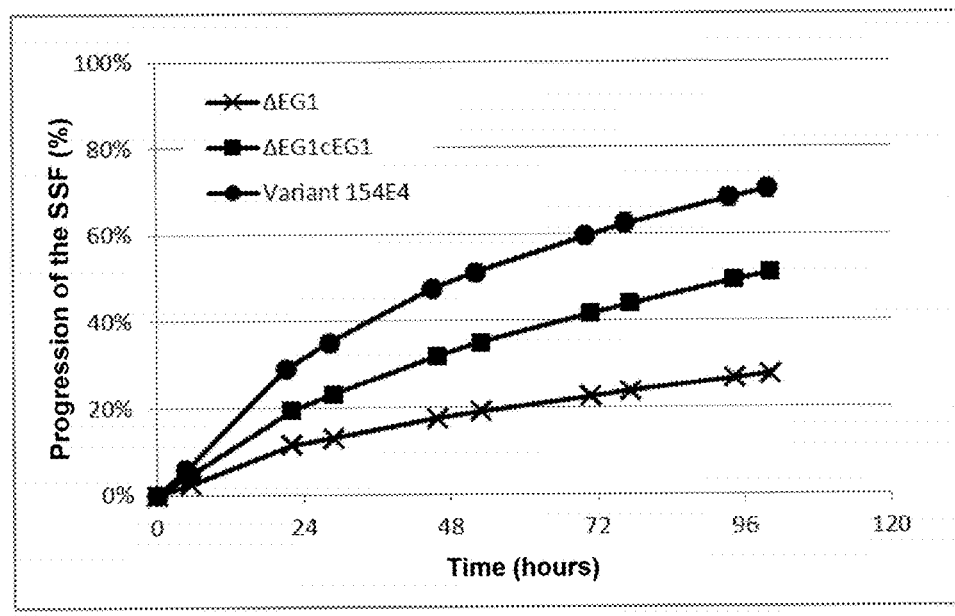
FIG. 4 is a graph presenting the results of SSF for the two cocktails derived from the strains 154E4/2 and 154E4/8 (SEQ ID NO: 10), a reference cocktail produced by the strain CL847 ΔEG1 (ΔEG1) supplemented with β-glucosidase and another reference cocktail produced by the strain CL847 ΔEG1 retransformed with the EG1 reference gene (ΔEG1cEG1) supplemented with β-glucosidase.

FIG. 4 presents the results of SSF for the 2 cocktails expressing the 154E4 endoglucanase (average of the results obtained with the 2 variants).

The results presented in FIG. 4 show that the progression (ethanol production for the same dose of enzymes) of the SSF over the course of 100 hours for the 2 cocktails expressing the 154E4 endoglucanase is greater than those of the ΔEG1 and ΔEG1cEG1 reference cocktails.

Figure 5:
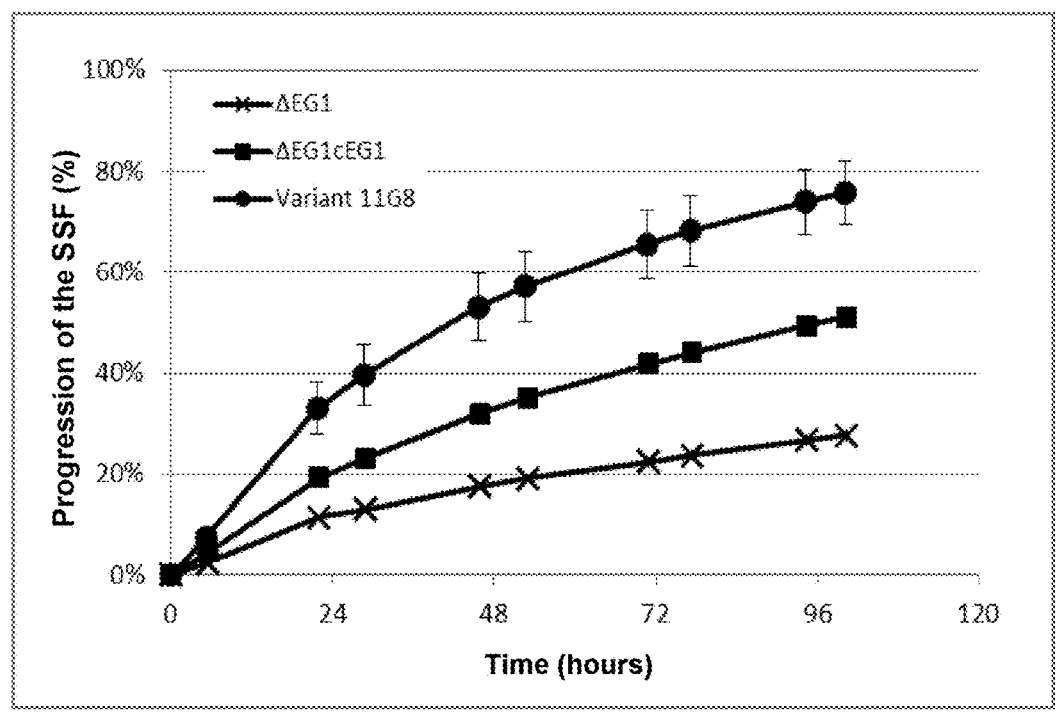
FIG. 5 is a graph presenting the results of SSF for the three cocktails derived from the strains 11G8/10, 11G8/12 and 11G8/13 (SEQ ID NO: 22), a reference cocktail produced by the strain CL847 ΔEG1 (ΔEG1) supplemented with β-glucosidase and another reference cocktail produced by the strain CL847 ΔEG1 retransformed with the EG1 reference gene (ΔEG1cEG1) supplemented with β-glucosidase.

FIG. 5 presents the results of SSF for the 3 cocktails expressing the 11G8 endoglucanase (average of the results obtained with the 2 variants).

The results presented in FIG. 5 show that the progression of the SSF over the course of 100 hours for the 3 cocktails expressing the 11G8 endoglucanase (average) is greater than those of the ΔEG1 and ΔEG1cEG1 reference cocktails.

The invention claimed is:

1. An isolated or purified polypeptide having an improved endoglucanase (EG) activity at 35° C. compared with the endoglucanase activity of the EG1 reference protein of SEQ ID NO:2, said polypeptide consists of:
  i) an amino acid sequence chosen from the group consisting of SEQ ID NO: 6, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24 and SEQ ID NO: 26; and
  ii) an amino acid sequence having, relative to the sequence SEQ ID NO: 6, SEQ ID NO: 10, SEQ ID NO: 18, SEQ ID NO: 20, SEQ ID NO: 22, SEQ ID NO: 24 or SEQ ID NO: 26, a percentage identity of at least 90%.

2. A purified or isolated nucleic acid encoding at least one polypeptide as claimed in claim 1.

3. The purified or isolated nucleic acid as claimed in claim 2, chosen from the following sequences: SEQ ID NO: 5, SEQ ID NO: 7, SEQ ID NO: 9, SEQ ID NO: 11; SEQ ID NO: 13, SEQ ID NO: 15, SEQ ID NO: 17, SEQ ID NO: 19, SEQ ID NO: 21, SEQ ID NO: 23 and SEQ ID NO: 25.

4. A vector comprising a nucleic acid as claimed in claim 2.

5. An isolated host cell comprising the nucleic acid as claimed in claim 2.

6. The isolated host cell as claimed in claim 5, wherein the host cell is selected from the group consisting of *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisae, Myceliophthora thermopila, Chrysosporium lucknowense, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae*.

7. The isolated host cell as claimed in claim 5, wherein the host cell is selected from the group consisting of *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisae, Myceliophthora thermopila, Chrysosporium lucknowense, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae*.

8. A method for hydrolyzing cellulose comprising contacting cellulose with a composition of at least one polypeptide of claim 1.

9. An enzymatic composition capable of acting on lignocellulosic biomass, said enzymatic composition being produced by filamentous fungi and comprising at least one polypeptide as claimed in claim 1.

10. A process for producing biofuel from biomass, wherein the process comprises the following successive steps:
  suspension, in an aqueous phase, of the biomass to be hydrolyzed;
  hydrolysis, in the presence of an enzymatic composition as claimed in claim 9, of the lignocellulosic biomass so as to produce a hydrolysate containing glucose;
  fermentation of the glucose of the hydrolysate so as to produce a fermentation must;
  separation of the biofuel from the fermentation must.

11. A process for producing biofuel from biomass, wherein the process comprises the following successive steps:
  suspension, in an aqueous phase, of the biomass to be hydrolyzed;
  simultaneous addition of an enzymatic composition as claimed in claim 10 and of a fermentative organism so as to produce a fermentation must;
  separation of the biofuel from the fermentation must.

12. The process as claimed in claim 11, wherein the fermentative organism is chosen from a host cell comprising a nucleic acid encoding for at least one isolated or purified polypeptide having improved endoglucanase activity compared with the endoglucanase activity of the EG1 reference protein, said polypeptide consisting of:
  i) an amino acid sequence chosen from the group consisting of SEQ ID NO: 6, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24 and SEQ ID NO: 26; and
  ii) an amino acid sequence having, relative to the sequence SEQ ID NO: 6, SEQ ID NO: 10, SEQ ID NO: 18, SEQ ID NO: 20, SEQ ID NO: 22, SEQ ID NO: 24 or SEQ ID NO: 26, a percentage identity of at least 90%.

13. A process for producing biofuel from biomass, comprising the following successive steps:
  suspending, in an aqueous phase, the biomass to be hydrolyzed;
  adding
    one or more host cells comprising the nucleic acid encoding for at least one isolated or purified polypeptide having an improved endoglucanase activity 35° C. compared with the endoglucanase activity of the EG1 reference protein of SEQ ID NO:2, said polypeptide consists of:
      i) an amino acid sequence chosen from the group consisting of SEQ ID NO: 6, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24 and SEQ ID NO: 26; and
      ii) an amino acid sequence having, relative to the sequence SEQ ID NO: 6, SEQ ID NO: 10SEQ ID NO: 18, SEQ ID NO: 20, SEQ ID NO: 22, SEQ ID NO: 24 or SEQ ID NO: 26, a percentage identity of at least 90%,
    with a fermentative organism and/or an enzymatic composition capable of acting on lignocellulosic biomass, said enzymatic composition being produced by filamentous fungi and comprising at least one isolated or purified polypeptide having an improved endoglucanase activity at 35° C. compared with the endoglucanase activity of the EG1 reference protein of SEQ ID NO:2, said polypeptide consists of:
      i) an amino acid sequence chosen from the group consisting of SEQ ID NO: 6, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24 and SEQ ID NO: 26; and
      ii) an amino acid sequence having, relative to the sequence SEQ ID NO: 6SEQ ID NO: 10SEQ ID NO: 18, SEQ ID NO: 20, SEQ ID NO: 22, SEQ ID NO: 24 or SEQ ID NO: 26, a percentage identity of at least 90% , so as to produce a fermentation must;

separating the biofuel from the fermentation must.

14. An isolated host cell comprising the vector as claimed in claim 4.

15. A vector comprising the nucleic acid as claimed in claim 3.

16. An isolated host cell as claimed in claim 6, wherein the host cell is selected from the group consisting of *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisae, Myceliophthora thermopila, Chrysosporium lucknowense, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae*.

* * * * *